US010945740B2

(12) United States Patent
Foshee et al.

(10) Patent No.: US 10,945,740 B2
(45) Date of Patent: Mar. 16, 2021

(54) SURGICAL CLIP

(71) Applicant: TELEFLEX MEDICAL INCORPORATED, Morrisville, NC (US)

(72) Inventors: David Lee Foshee, Apex, NC (US); Michael Dell Ramsey, Raleigh, NC (US)

(73) Assignee: TELEFLEX MEDICAL INCORPORATED, Morrisville, NC (US)

(*) Notice: Subject to any disclaimer, the term of this patent is extended or adjusted under 35 U.S.C. 154(b) by 103 days.

(21) Appl. No.: 16/016,022

(22) Filed: Jun. 22, 2018

(65) Prior Publication Data
US 2018/0368852 A1 Dec. 27, 2018

Related U.S. Application Data

(60) Provisional application No. 62/675,383, filed on May 23, 2018, provisional application No. 62/523,562, filed on Jun. 22, 2017.

(51) Int. Cl.
*A61B 17/122* (2006.01)
*A61B 17/04* (2006.01)
*A61B 17/00* (2006.01)

(52) U.S. Cl.
CPC ........ *A61B 17/122* (2013.01); *A61B 17/0487* (2013.01); *A61B 17/0482* (2013.01); *A61B 2017/00778* (2013.01); *A61B 2017/00955* (2013.01)

(58) Field of Classification Search
CPC .................. A61B 17/0487; A61B 17/122
See application file for complete search history.

(56) References Cited

U.S. PATENT DOCUMENTS

| 1,728,322 | A | 9/1929 | Badrian |
| 2,635,238 | A | 4/1953 | Mather |
| 3,171,184 | A | 3/1965 | Wilhelm |
| 3,503,397 | A | 3/1970 | Fogarty et al. |
| 3,766,925 | A | 10/1973 | Rubricius |
| 3,825,012 | A | 7/1974 | Nicoll |
| 3,867,944 | A | 2/1975 | Samuels |
| 3,874,042 | A | 4/1975 | Eddleman et al. |
| 4,337,774 | A | 7/1982 | Perlin |

(Continued)

FOREIGN PATENT DOCUMENTS

| CN | 101543418 A | 9/2009 |
| CN | 105054989 A | 11/2015 |

(Continued)

*Primary Examiner* — Gregory A Anderson
(74) *Attorney, Agent, or Firm* — BakerHostetler

(57) ABSTRACT

A surgical clip may include: a first leg member having an inner surface, an outer surface, and first and second side surfaces, the inner surface of the first leg member having a concave curvature; a second leg member having an inner surface, an outer surface, and first and second side surfaces, the inner surface of the second leg member having a convex curvature; at least one first tooth extending from a first lateral side of the inner surface of the second leg member; and a first channel defined between the first side surface and the inner surface of the first leg member. The first and second leg members may be configured to move between an open configuration and a closed configuration, and in the closed configuration, the at least one first tooth is received in the first channel.

28 Claims, 12 Drawing Sheets

(56) References Cited

U.S. PATENT DOCUMENTS

| | | |
|---|---|---|
| 4,340,061 A | 7/1982 | Kees, Jr. et al. |
| 4,345,600 A | 8/1982 | Rothfuss |
| 4,346,869 A | 8/1982 | MacNeill |
| 4,390,019 A | 6/1983 | LeVeen et al. |
| 4,418,694 A | 12/1983 | Beroff et al. |
| 4,450,840 A | 5/1984 | Mericle et al. |
| 4,458,682 A | 7/1984 | Cerwin |
| 4,476,865 A | 10/1984 | Failla et al. |
| 4,487,205 A | 12/1984 | Di Giovanni et al. |
| 4,519,392 A | 5/1985 | Lingua |
| 4,527,562 A | 7/1985 | Mericle |
| 4,550,729 A | 11/1985 | Cerwin et al. |
| 4,579,118 A | 4/1986 | Failla |
| 4,588,160 A | 5/1986 | Flynn et al. |
| 4,589,626 A | 5/1986 | Kurtz et al. |
| 4,638,804 A | 1/1987 | Jewusiak |
| 4,712,549 A | 12/1987 | Peters et al. |
| 4,716,886 A | 1/1988 | Schulman et al. |
| 4,726,372 A | 2/1988 | Perlin |
| 4,807,622 A | 2/1989 | Ohkaka et al. |
| 4,822,348 A | 4/1989 | Casey |
| 4,834,096 A | 5/1989 | Oh et al. |
| 4,870,965 A | 10/1989 | Jahanger |
| 4,936,447 A | 6/1990 | Peiffer |
| 4,938,765 A | 7/1990 | Rasmusson |
| 4,942,886 A | 7/1990 | Timmons |
| 4,950,275 A | 8/1990 | Donini |
| 4,955,897 A | 9/1990 | Ship |
| 4,961,499 A | 10/1990 | Kulp |
| 4,972,949 A | 11/1990 | Peiffer |
| 4,976,722 A | 12/1990 | Failla |
| 5,002,552 A | 3/1991 | Casey |
| 5,009,657 A | 4/1991 | Cotey et al. |
| 5,026,382 A | 6/1991 | Peiffer |
| 5,046,611 A | 9/1991 | Oh |
| 5,047,038 A | 9/1991 | Peters et al. |
| 5,062,846 A | 11/1991 | Oh et al. |
| 5,078,731 A | 1/1992 | Hayhurst |
| 5,100,416 A | 3/1992 | Oh et al. |
| 5,104,395 A | 4/1992 | Thornton et al. |
| 5,112,343 A | 5/1992 | Thornton |
| 5,127,915 A | 7/1992 | Mattson |
| 5,160,339 A | 11/1992 | Chen et al. |
| 5,171,251 A | 12/1992 | Bregen et al. |
| 5,171,252 A | 12/1992 | Friedland |
| 5,201,416 A | 4/1993 | Taylor |
| 5,234,449 A | 8/1993 | Bruker et al. |
| 5,259,405 A | 11/1993 | Hua-Chou |
| 5,279,416 A | 1/1994 | Malec et al. |
| 5,330,442 A | 7/1994 | Green et al. |
| 5,330,487 A | 7/1994 | Thornton et al. |
| 5,366,458 A | 11/1994 | Korthoff et al. |
| 5,366,459 A | 11/1994 | Yoon |
| 5,462,555 A | 10/1995 | Bolanos et al. |
| 5,487,746 A | 1/1996 | Yu et al. |
| 5,501,693 A | 3/1996 | Gravener |
| 5,509,920 A | 4/1996 | Phillips et al. |
| 5,549,621 A | 8/1996 | Bessler et al. |
| 5,575,802 A | 11/1996 | McQuilkin et al. |
| 5,626,592 A | 5/1997 | Philips |
| 5,667,516 A | 9/1997 | Allen |
| 5,697,938 A | 12/1997 | Jensen et al. |
| 5,713,911 A | 2/1998 | Racenet et al. |
| 5,713,912 A | 2/1998 | Porter |
| 5,722,982 A | 3/1998 | Ferreira et al. |
| 5,725,542 A | 3/1998 | Yoon |
| 5,810,853 A | 9/1998 | Yoon |
| 5,846,255 A | 12/1998 | Casey |
| 5,908,430 A | 6/1999 | Appleby |
| 5,921,991 A | 7/1999 | Whitehead et al. |
| 5,925,052 A | 7/1999 | Simmons |
| 5,997,548 A | 12/1999 | Jahanger |
| 6,015,417 A | 1/2000 | Reynolds, Jr. |
| 6,099,539 A | 8/2000 | Howell |
| 6,131,576 A | 10/2000 | Davis |
| 6,206,896 B1 | 3/2001 | Howell |
| 6,210,419 B1 | 4/2001 | Mayenberger et al. |
| 6,217,590 B1 | 4/2001 | Levinson |
| 6,261,303 B1 | 7/2001 | Mayenberger et al. |
| 6,305,387 B1 | 10/2001 | Atchison |
| 6,349,727 B1 | 2/2002 | Stewart, Jr. |
| 6,387,106 B1 | 5/2002 | Howell |
| 6,391,035 B1 | 5/2002 | Appleby et al. |
| 6,419,682 B1 | 7/2002 | Appleby et al. |
| 6,537,289 B1 | 3/2003 | Kayan et al. |
| 6,638,282 B2 | 10/2003 | Ramsey |
| 6,699,258 B1 | 3/2004 | Sadler et al. |
| 6,719,766 B1 | 4/2004 | Buelna et al. |
| 6,824,547 B2 | 11/2004 | Wilson, Jr. et al. |
| 6,843,253 B2 | 1/2005 | Parkes |
| 6,863,675 B2 | 3/2005 | Wilson, Jr. |
| 6,880,699 B2 | 4/2005 | Gallagher |
| 6,989,017 B2 | 1/2006 | Howell et al. |
| 7,001,412 B2 | 2/2006 | Gallagher et al. |
| 7,052,504 B2 | 5/2006 | Hughett |
| 7,131,977 B2 | 11/2006 | Fowler |
| 7,211,091 B2 | 5/2007 | Fowler et al. |
| 7,211,092 B2 | 5/2007 | Hughett |
| 7,316,696 B2 | 1/2008 | Wilson, Jr. et al. |
| 7,326,223 B2 | 2/2008 | Wilson, Jr. |
| 7,329,266 B2 | 2/2008 | Royse et al. |
| 7,402,164 B2 | 7/2008 | Watson, Jr. et al. |
| 7,585,304 B2 | 9/2009 | Hughett |
| 7,635,374 B2 | 12/2009 | Monassevitch et al. |
| 7,645,285 B2 | 1/2010 | Cosgrove et al. |
| 7,892,244 B2 | 2/2011 | Monassevitch et al. |
| 7,963,964 B2 | 6/2011 | Santilli et al. |
| 7,992,757 B2 | 8/2011 | Wheeler et al. |
| 8,137,368 B2 | 3/2012 | Kayan et al. |
| 8,262,639 B2 | 9/2012 | Mathias |
| 9,084,596 B2 | 7/2015 | Stanley et al. |
| 9,220,507 B1 | 12/2015 | Patel et al. |
| 9,282,972 B1 | 3/2016 | Patel et al. |
| 9,445,820 B2 | 9/2016 | Whiting |
| 9,456,824 B2 | 10/2016 | Willett et al. |
| 9,855,053 B2 | 1/2018 | Bagaoisan et al. |
| 10,201,353 B2 | 2/2019 | Menn |
| 10,265,079 B2 | 4/2019 | Brodaczewski et al. |
| 10,384,049 B2 | 8/2019 | Stanton et al. |
| 2002/0068946 A1 | 6/2002 | Kortenbach et al. |
| 2002/0111640 A1 | 8/2002 | Krause et al. |
| 2002/0169459 A1 | 11/2002 | Porat |
| 2002/0183785 A1 | 12/2002 | Howell et al. |
| 2003/0074009 A1 | 4/2003 | Ramsey et al. |
| 2004/0059359 A1 | 3/2004 | Wilson, Jr. |
| 2004/0172043 A1 | 9/2004 | Watson, Jr. et al. |
| 2005/0149069 A1 | 7/2005 | Bertolero et al. |
| 2005/0165421 A1 | 7/2005 | Wilson, Jr. et al. |
| 2005/0165422 A1 | 7/2005 | Wilson |
| 2005/0165423 A1 | 7/2005 | Gallagher et al. |
| 2005/0165424 A1 | 7/2005 | Gallagher et al. |
| 2005/0165429 A1 | 7/2005 | Douglas et al. |
| 2006/0217749 A1 | 9/2006 | Wilson et al. |
| 2007/0083218 A1 | 4/2007 | Morris |
| 2007/0118161 A1 | 5/2007 | Kennedy et al. |
| 2007/0149989 A1 | 6/2007 | Santilli et al. |
| 2007/0213585 A1 | 9/2007 | Monassevitch et al. |
| 2007/0213747 A1 | 9/2007 | Monassevitch et al. |
| 2007/0276417 A1 | 11/2007 | Mendes, Jr. et al. |
| 2008/0039879 A1 | 2/2008 | Chin et al. |
| 2008/0045981 A1 | 2/2008 | Margolin et al. |
| 2008/0208324 A1 | 8/2008 | Glithero et al. |
| 2008/0287976 A1 | 11/2008 | Weaner et al. |
| 2008/0312670 A1 | 12/2008 | Lutze et al. |
| 2009/0012545 A1 | 1/2009 | Williamson et al. |
| 2009/0171380 A1 | 7/2009 | Whiting |
| 2009/0240266 A1 | 9/2009 | Dennis |
| 2010/0114131 A1 | 5/2010 | Rotunda |
| 2010/0211080 A1 | 8/2010 | Kennedy et al. |
| 2010/0274268 A1 | 10/2010 | Singh et al. |
| 2010/0331862 A1 | 12/2010 | Monassevitch et al. |

(56) References Cited

U.S. PATENT DOCUMENTS

| | | |
|---|---|---|
| 2011/0022079 A1 | 1/2011 | Miles et al. |
| 2011/0112559 A1 | 5/2011 | Monassevitch et al. |
| 2011/0245848 A1 | 10/2011 | Rosenberg et al. |
| 2011/0270285 A1 | 11/2011 | Lissa |
| 2011/0295291 A1 | 12/2011 | Trivisani |
| 2012/0083803 A1 | 4/2012 | Patel et al. |
| 2013/0006271 A1 | 1/2013 | Vold et al. |
| 2013/0226200 A1 | 8/2013 | Kappel et al. |
| 2013/0261642 A1 | 10/2013 | Willett et al. |
| 2014/0018832 A1 | 1/2014 | Shelton |
| 2014/0058411 A1 | 2/2014 | Soutourine et al. |
| 2014/0243862 A1 | 8/2014 | Bagaoisan et al. |
| 2016/0174981 A1 | 6/2016 | Fago et al. |
| 2016/0354089 A1 | 12/2016 | Whiting |
| 2017/0009895 A1 | 1/2017 | Stanton et al. |
| 2017/0209151 A1 | 7/2017 | Brown |
| 2017/0311954 A1 | 11/2017 | Brodaczewski et al. |
| 2018/0036008 A1 | 2/2018 | Ramsey et al. |
| 2018/0168659 A1 | 6/2018 | Bagaoisan et al. |
| 2018/0221029 A1 | 8/2018 | Menn |
| 2019/0314025 A1 | 10/2019 | Patel et al. |
| 2019/0314031 A1 | 10/2019 | Thomas et al. |
| 2020/0046359 A1 | 2/2020 | Thomas et al. |

FOREIGN PATENT DOCUMENTS

| | | |
|---|---|---|
| EP | 0086640 A2 | 8/1983 |
| EP | 0122046 A1 | 10/1984 |
| EP | 0314064 A2 | 5/1989 |
| EP | 0201344 B1 | 12/1989 |
| EP | 1233705 B1 | 1/2008 |
| EP | 2074954 B1 | 8/2011 |
| GB | 2069848 A | 9/1981 |
| GB | 2353710 A | 3/2001 |
| GB | 2465560 A | 5/2010 |
| JP | 56-151034 A | 11/1981 |
| JP | S61-259652 A | 11/1986 |
| JP | H03-178648 A | 8/1991 |
| JP | 2002-345828 A | 12/2002 |
| WO | 2006/102578 A1 | 9/2006 |
| WO | 2012/075532 A1 | 6/2012 |
| WO | 2016205343 A1 | 12/2016 |
| WO | 2019/099462 A1 | 5/2019 |
| WO | 2019169580 A1 | 9/2019 |

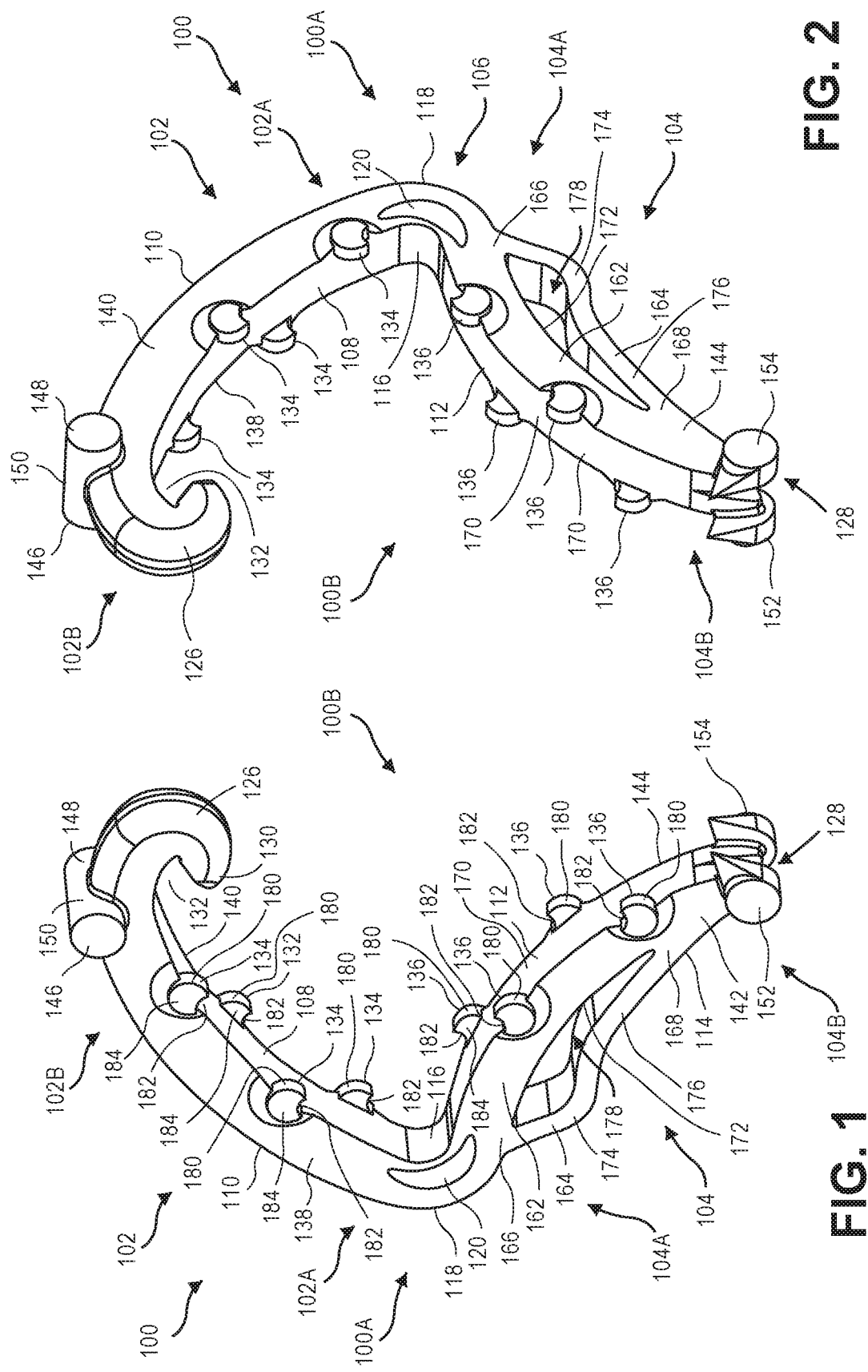

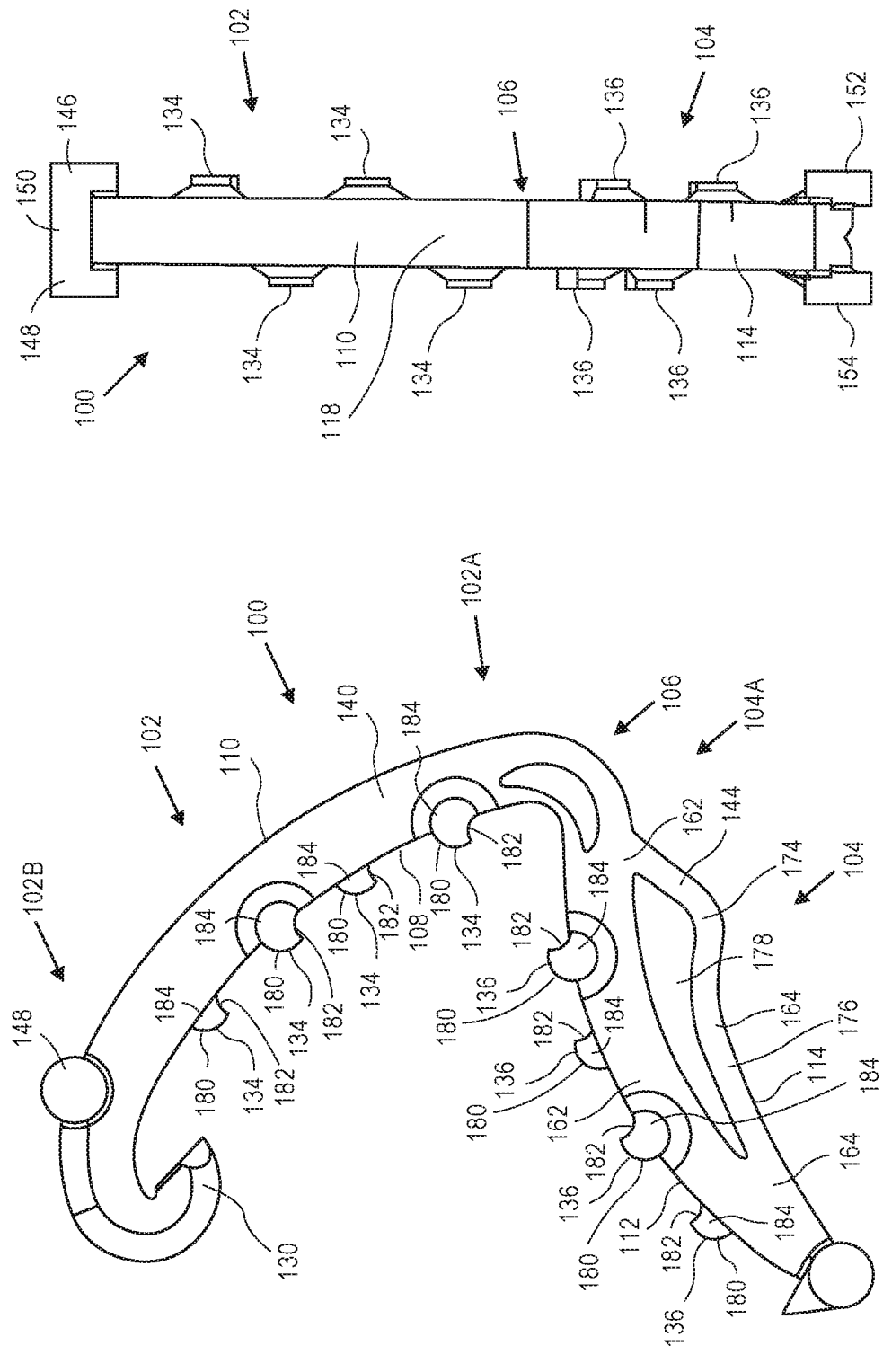

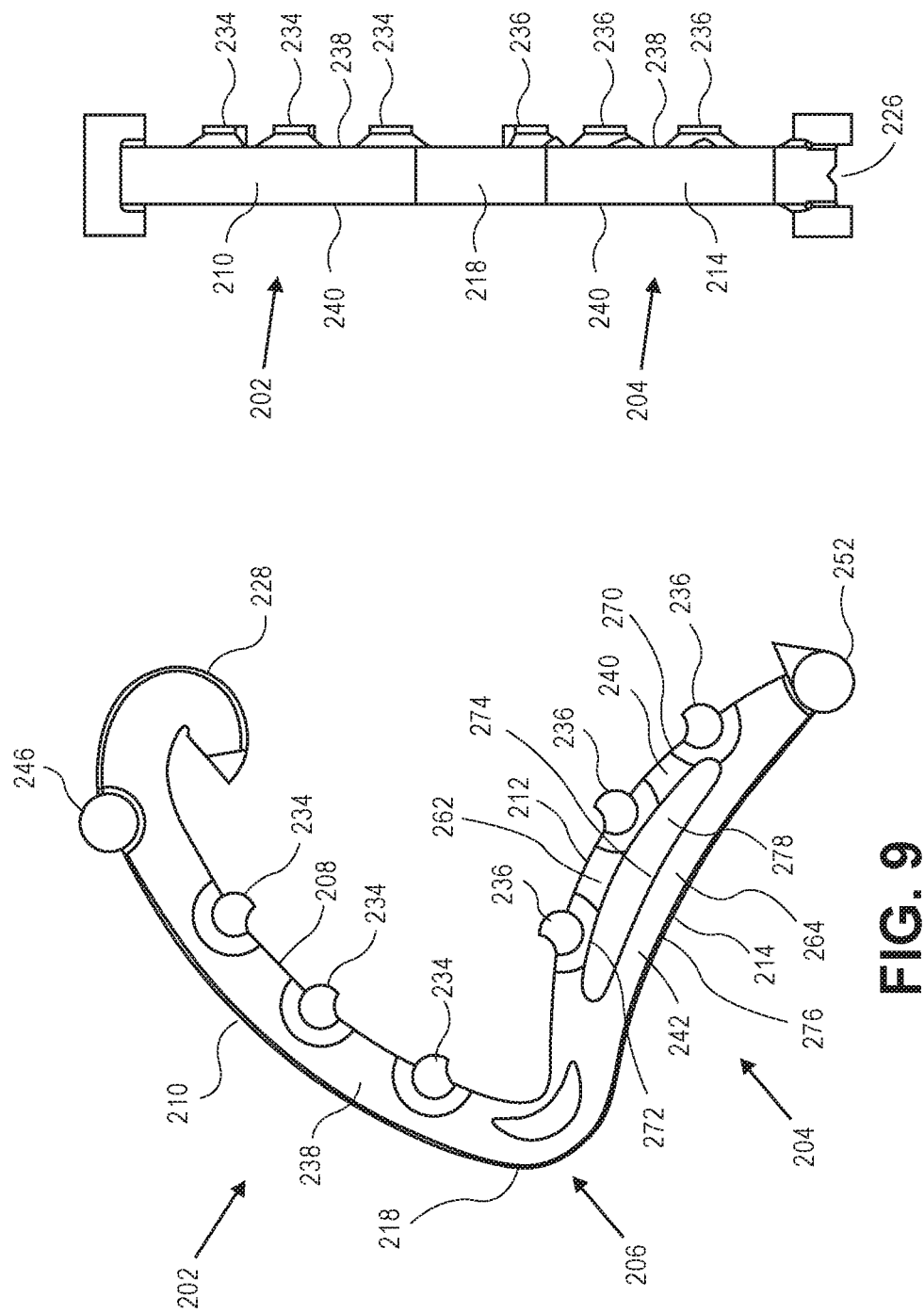

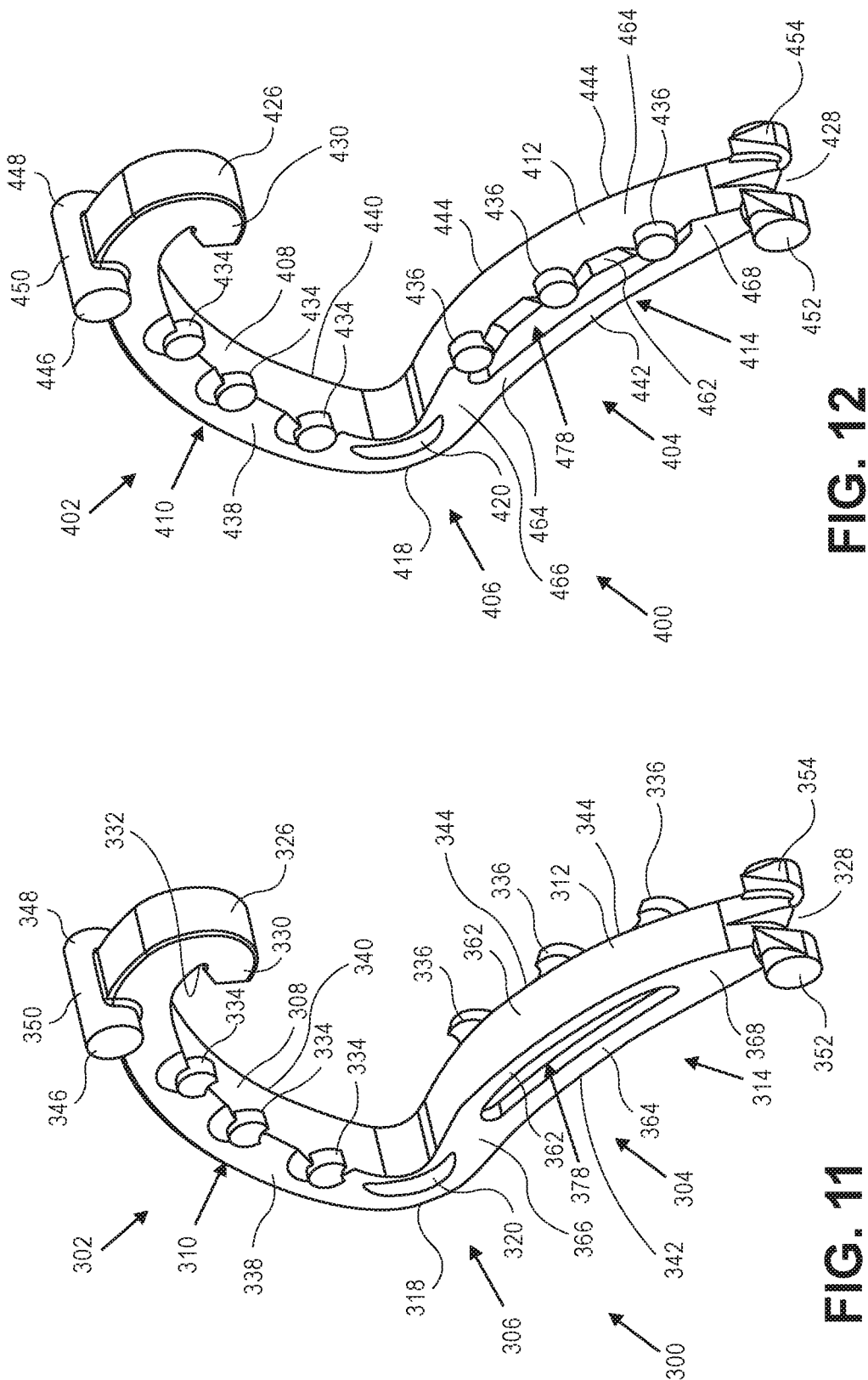

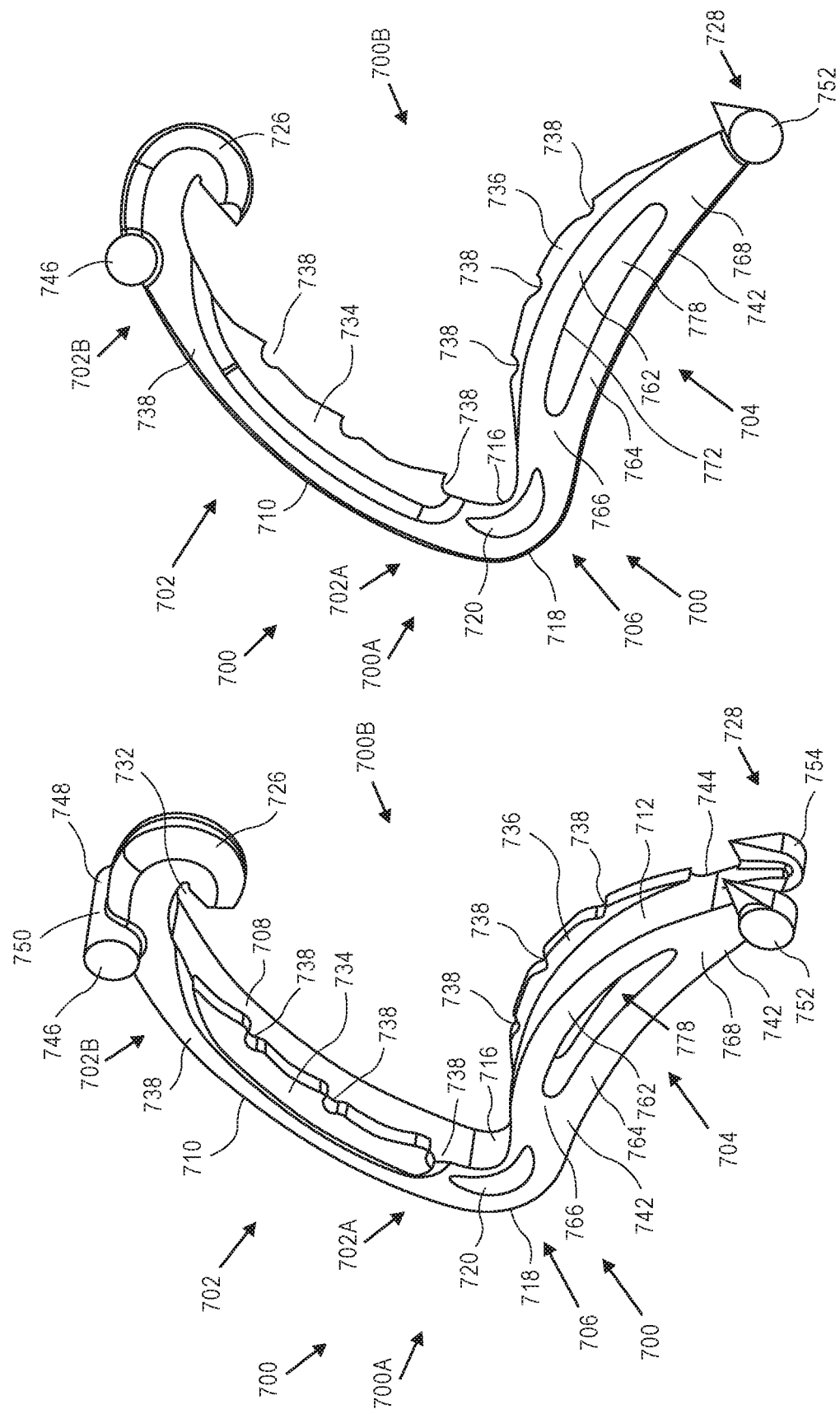

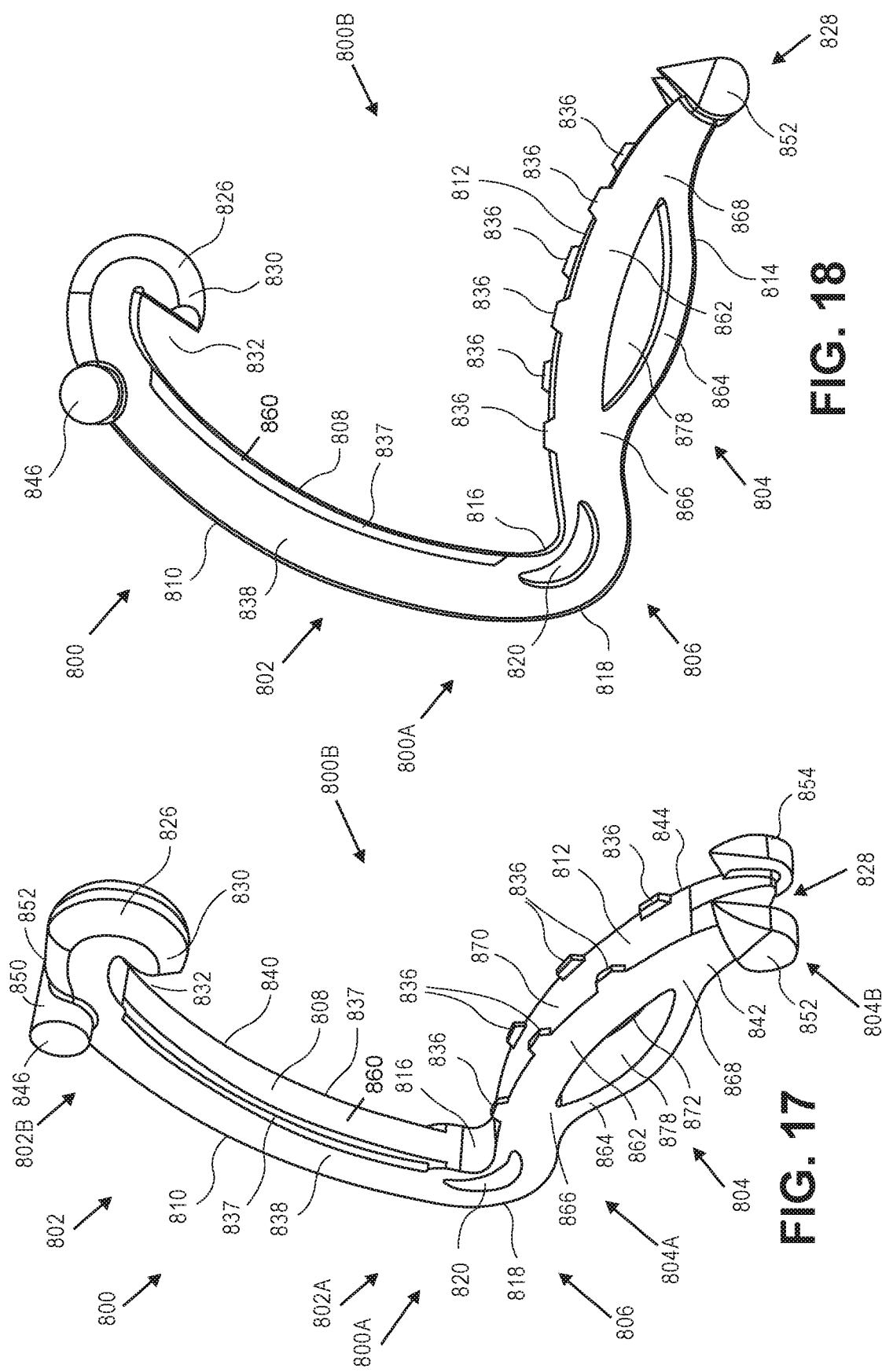

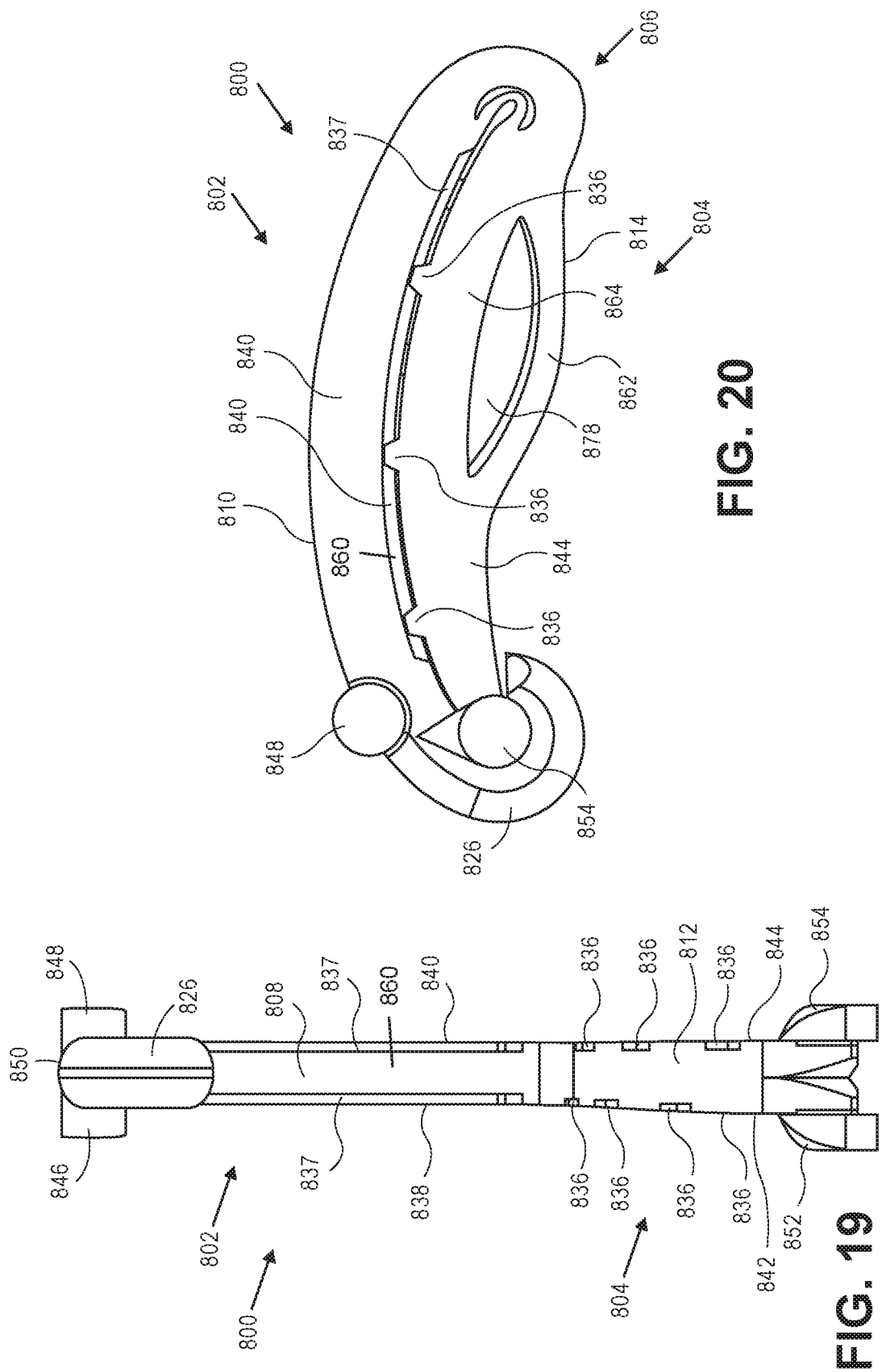

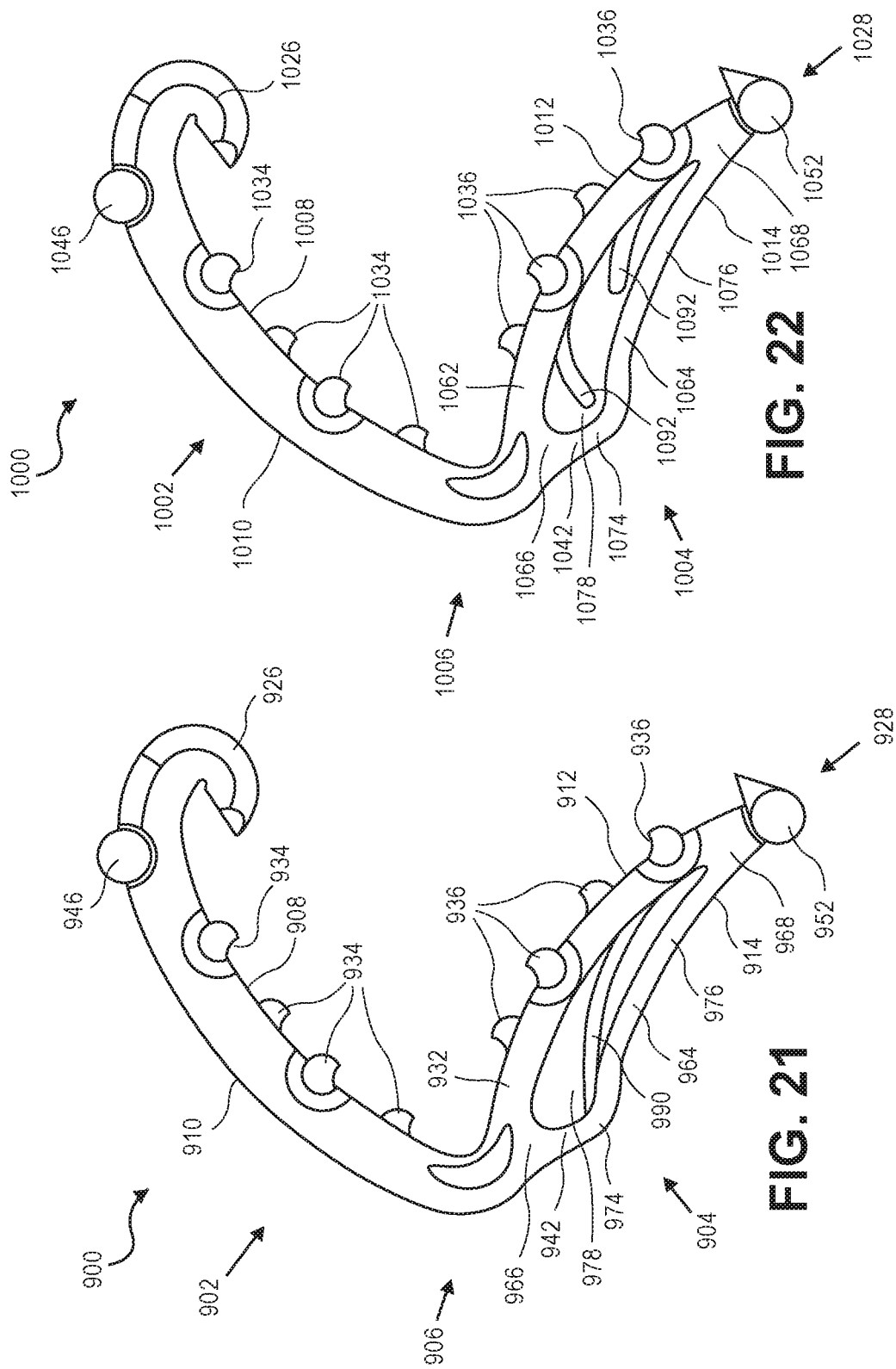

SURGICAL CLIP

PRIORITY

The present Non-Provisional Patent Application claims priority to U.S. Provisional Patent Application No. 62/523,562, filed on Jun. 22, 2017 and now expired, and U.S. Provisional Patent Application No. 62/675,383, filed on May 23, 2018 and now expired, the entire disclosures of which are incorporated herein.

TECHNICAL FIELD

The present invention relates generally to medical devices, and more particularly, to surgical clips for ligation of tissue.

BACKGROUND

Ligation of tissue (e.g., blood vessels, lymph nodes, nerves, cystic ducts, and cardiac tissue) is a common practice for many surgical procedures. This can be performed by closing the vessel with a surgical clip or by suturing the vessel with the surgical thread. The use of surgical thread requires complex manipulations of a needle and surgical thread to form knots required to secure the vessel. Such complex manipulations are time consuming and difficult to perform, particularly in endoscopic surgical procedures characterized by limited space and/or visibility. In contrast, surgical clips are relatively quick and easy to apply. Accordingly, the use of surgical clips in endoscopic and open surgical procedures has grown dramatically.

SUMMARY

The present inventors recognize that there is a need to improve one or more features of the surgical clips, such as the closure of small vessels. Current surgical clips are often provided with teeth extending between tissue engaging surfaces that may not sufficiently engage and/or compress small vessels. The teeth often interfere with the approximation or contact of the clamping surfaces and prevent full closure of the surgical clip. Furthermore, current surgical clips often apply a non-uniform pressure distribution on the compressed tissue. For example, current surgical clips are often provided with substantially rigid leg members that do not sufficiently conform to different sizes of tissue, causing stress localization. The non-uniform pressure distribution may result in tissue damage and/or rupture, especially with overstressed, fibrotic, and/or infarcted tissue. The disclosed devices and methods are directed to mitigating or overcoming one or more of the problems set forth above and/or other problems in the prior art.

A first aspect of the present invention is directed to a surgical clip. The surgical clip may include a first leg member having a first inner surface, a first outer surface, and a first side surface. The first inner surface may have a concave curvature. The surgical clip may also include a second leg member having a second inner surface, a second outer surface, and a second side surface. The second inner surface may have a convex curvature. The surgical clip may further include at least one first tooth positioned on the first leg member and at least one second tooth positioned on the second leg member. The at least one first tooth may be attached to the first side surface laterally of the first inner surface, and the at least one second tooth may be attached to the second side surface laterally of the second inner surface. The first and second leg members may be configured to move between an open configuration and a closed configuration. In the closed configuration, the at least one first tooth may be configured to extend along the second side surface laterally of the second inner surface, and the at least one second tooth may be configured to extend along the first side surface laterally of the first inner surface.

A second aspect of the present invention is directed to a surgical clip. The surgical clip may include a first leg member having a first inner surface and a first outer surface. The surgical clip may also include a second leg member having a second inner surface, a second outer surface, an inner portion, and an outer portion. The inner portion may at least partially form the second inner surface and have a first radius of curvature. The outer portion may at least partially form the second outer surface and have a second radius of curvature that is different than the first radius of curvature.

A third aspect of the present invention is directed to a surgical clip. The surgical clip may include a first leg member having a first inner surface, a first outer surface, and a first side surface, the first inner surface having a concave curvature. The surgical clip may also include a second leg member having a second inner surface, a second outer surface, and a second side surface, the second inner surface having a convex curvature. The second leg member may further include an inner portion and an outer portion separated by a transverse channel. The inner portion may at least partially form the second inner surface and having a first radius of curvature, and the outer portion may have a second radius of curvature, where the second radius of curvature is different than the first radius of curvature for substantially the entire length of the inner and outer portions. The surgical clip may also include at least one first tooth positioned on the first leg member and at least one second tooth positioned on the second leg member. The first and second leg members may be configured to move between an open configuration and a closed configuration. In the closed configuration, the at least one first tooth may be configured to extend along the second side surface laterally of the second inner surface, and the at least one second tooth may be configured to extend along the first side surface laterally of the first inner surface.

A fourth aspect of the present invention is directed to a surgical clip. The surgical clip may include a first leg member having an inner surface, an outer surface, and first and second side surfaces, the inner surface of the first leg member having a concave curvature. The surgical clip may also include a second leg member having an inner surface, an outer surface, and first and second side surfaces, the inner surface of the second leg member having a convex curvature. The surgical clip may further include at least one tooth extending from a first lateral side of the inner surface of the second leg member, and a channel in the first side surface of the first leg member. The first and second leg members may be configured to move between an open configuration and a closed configuration, and in the closed configuration, the at least one tooth may be received in the channel.

A fifth aspect of the present invention is directed to a surgical clip. The surgical clip may include a first leg member having an inner surface and an outer surface, the inner surface of the first leg member having a concave curvature, and the outer surface of the first leg member having a convex curvature. The surgical clip may also include a second leg member having an inner surface, an outer surface, an inner portion, and an outer portion, the inner surface of the second leg member having a convex curvature, and the outer surface of the second leg member having a convex curvature. The inner portion and the outer portion may be separated by a transverse channel through the second leg member. The inner portion may at least partially form the convex curvature of the inner surface of the second leg member, and the outer portion may at least partially form the convex curvature of the outer surface of the second leg member.

A sixth aspect of the present invention is directed to a surgical clip. A surgical clip may include: a first leg member having an inner surface, an outer surface, and first and second side surfaces, the inner surface of the first leg member having a concave curvature; a second leg member having an inner surface, an outer surface, and first and second side surfaces, the inner surface of the second leg member having a convex curvature; at least one first tooth extending from a first lateral side of the inner surface of the second leg member; and a first channel defined between the first side surface and the inner surface of the first leg member. The first and second leg members may be configured to move between an open configuration and a closed configuration, and in the closed configuration, the at least one first tooth is received in the first channel.

A seventh aspect of the present invention is directed to a surgical clip. The surgical clip may include a first leg member having an inner surface and an outer surface, the inner surface of the first leg member having a concave curvature, and the outer surface of the first leg member having a convex curvature. The surgical clip may include a second leg member having an inner surface, an outer surface, an inner portion, and an outer portion, the inner surface of the second leg member having a convex curvature, and the outer surface of the second leg member having a convex curvature. The surgical clip may include at least one tooth extending from a first lateral side of the inner surface of the second leg member, and a channel in the first side surface of the first leg member. The inner portion and the outer portion may be separated by a transverse channel through the second leg member. The inner portion may at least partially form the convex curvature of the inner surface of the second leg member, and the outer portion may at least partially form the convex curvature of the outer surface of the second leg member. The first and second leg members may be configured to move between an open configuration and a closed configuration, and in the closed configuration, the at least one tooth may be received in the channel.

BRIEF DESCRIPTION OF THE DRAWINGS

In order that the invention may be readily understood, aspects of this invention are illustrated by way of examples in the accompanying drawings.

FIG. 1 illustrates a first perspective view of a first exemplary embodiment of a surgical clip of the present invention.

FIG. 2 illustrates a second perspective view of the first exemplary embodiment of the surgical clip of FIG. 1.

FIG. 3 illustrates a side view of the first exemplary embodiment of the surgical clip of FIGS. 1 and 2.

FIG. 4 illustrates a rear view of the first exemplary embodiment of the surgical clip of FIGS. 1-3.

FIG. 9 illustrates a side view of the second exemplary embodiment of the surgical clip of FIGS. 7 and 8.

FIG. 10 illustrates a rear view of the second exemplary embodiment of the surgical clip of FIGS. 7-9.

FIG. 11 illustrates a perspective view of a third exemplary embodiment of the surgical clip of the present invention.

FIG. 12 illustrates a perspective view of a fourth exemplary embodiment of the surgical clip of the present invention.

FIG. 15 illustrates a perspective view of a seventh exemplary embodiment of the surgical clip of the present invention.

FIG. 16 illustrates a side view of the seventh exemplary embodiment of the surgical clip of FIG. 15.

FIG. 17 illustrates a perspective view of an eighth exemplary embodiment of the surgical clip of the present invention.

FIG. 18 illustrates a side view of the eighth exemplary embodiment of the surgical clip of FIG. 17.

FIG. 19 illustrates a front view of the eighth exemplary embodiment of the surgical clip of FIGS. 17 and 18.

FIG. 20 illustrates a side view of an exemplary closed configuration of the eighth exemplary embodiment of the surgical clip of FIGS. 17-19.

FIG. 21 illustrates a side view of an exemplary open configuration of a ninth exemplary embodiment of the surgical clip of the present invention.

FIG. 22 illustrates a side view of an exemplary open configuration of a tenth exemplary embodiment of the surgical clip of the present invention.

The same or similar reference numbers are used in the drawings and the following detailed description to refer to the same or similar parts.

DETAILED DESCRIPTION

Figure 5:
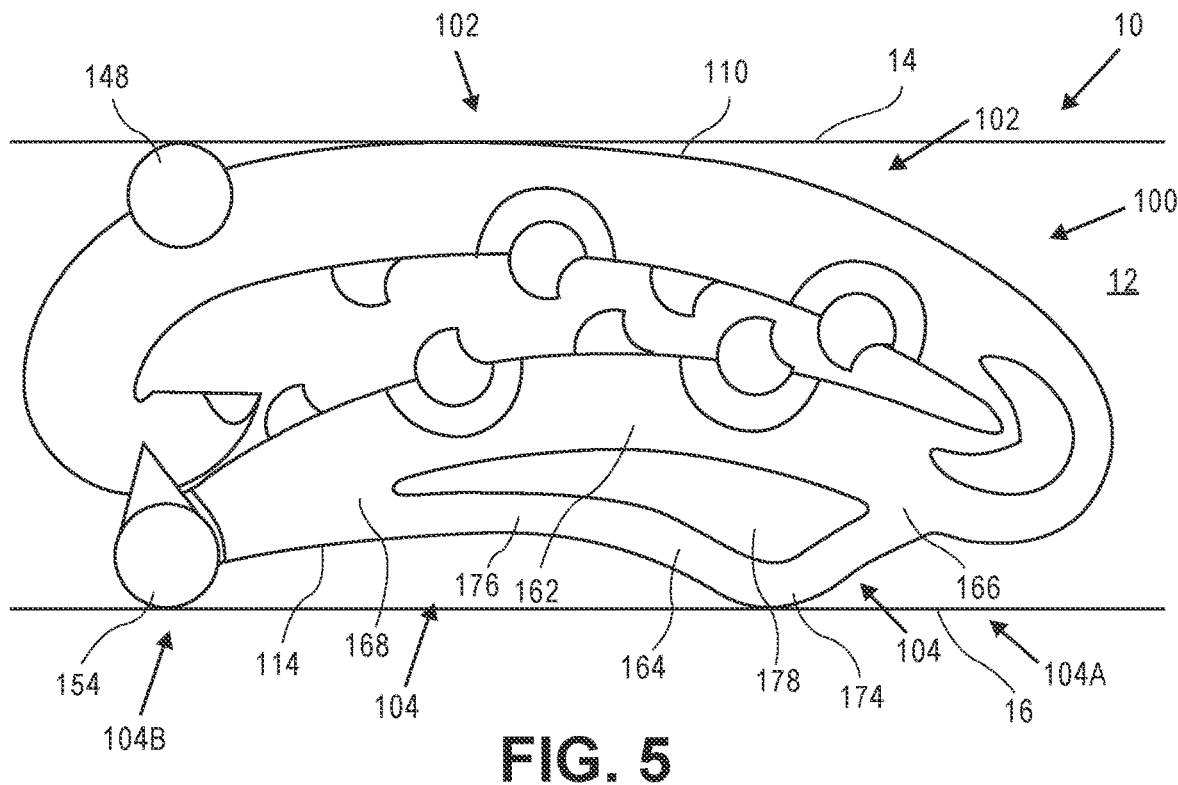
FIG. 5 illustrates a side view of a deflected configuration of the first exemplary embodiment of the surgical clip of FIGS. 1-4.

The invention will now be described with reference to the figures, in which like reference numerals may refer to like parts throughout. The present invention is generally directed to a surgical clip configured to compress and/or ligate tissue (e.g., blood vessels, lymph nodes, nerves, cystic tubes, or cardiac tissue). The surgical clip may comprise out-board teeth that do not impede full closure of the surgical clip, providing more effective occlusion of smaller vessels. In that sense, clamping surfaces may be substantially smooth, and the teeth may be spaced apart. The out-board teeth may also allow the teeth to be larger and more effective in tissue interaction. The out-board teeth may be easy to mold and not interfere with clip appliers. In some embodiments, the teeth may also be substantially atraumatic, such that the surgical clip would not pinch tissue between adjacent teeth. For example, the teeth may minimize sharp edges, and have substantially flat or convex inner surfaces, and substantially flat side surfaces. In some embodiments, the teeth may include a convex distal portion and a concave proximal portion. The concave proximal portion may be configured to improve tissue retention and prevent the tissue from slipping distally out of the surgical clip in a "watermelon-seeding" effect as the surgical clip closes.

The surgical clip may also include a first leg member having a concave inner surface, and a second leg member having a convex inner surface. The convex inner surface may be provided by a flexible inner portion configured to resiliently compress when the surgical clip engages tissue. The flexibility of the inner portion may enable favorable pressure distribution on tissue of different shapes, sizes, and/or stiffnesses, and/or tissue compressed at different positions along the length of the surgical clip. The inner portion may be spaced from an outer portion by a transverse channel, for example, in a split-leg configuration. The inner and outer portions may also have different radii of curvature. In some embodiments, the inner and outer portions may have different radii of curvature along at least half a length of the inner and outer portions. In some embodiments, the inner and outer portions may have different radii of curvature along substantially the entire length of the inner and outer portions. For example, the outer portion may include a convex portion having a convex outer surface and a concave portion having a concave outer surface. In some embodiments, the convex portion may be positioned on the proximal portion of the second leg member, providing the second leg member a proximal portion having a greater height than a distal portion. The height of the proximal portion may provide a contact point to improve alignment of the surgical clip as it is fed through a channel of a clip applier and/or received in the jaws of the clip applier. In some embodiments, the surgical clip may further include compression members extending between the inner and outer portions and being configured to improve compressive load distribution between the inner and outer portions as the surgical clip is compressed, while maintaining flexibility and accommodating the complex deformation that the surgical clip goes through to close and/or lock.

FIGS. 1-6 illustrate a first embodiment of a surgical clip 100 of the present invention. The surgical clip 100 may have a proximal end portion 100A and a distal end portion 100B. The surgical clip 100 may further include a first leg member 102 having a proximal end portion 102A and a distal end portion 102B, and a second leg member 104 having a proximal end portion 104A and a distal end portion 104B. The first and second leg members 102, 104 may be integrally joined at the proximal end portions 102A, 104A by a hinge portion 106.

In accordance with conventional practice, as used herein, and unless otherwise indicated herein, the term "proximal portion" refers to the specified portion of a device or its component which is generally closer to the medical personnel handling or manipulating the device as it is intended to be used, and the term "distal portion" refers to the specified portion of a device or its component which is opposite the proximal portion. The term "longitudinal" is directed to the dimension which extends along the length of the surgical clip 100 and/or leg members 102, 104 from their respective proximal end portions 100A, 102A, 104A to their respective distal end portions 100B, 102B, 104B, as would be commonly understood by one of skill in the art. Furthermore, as used herein, the "transverse" direction is directed to any axis or direction which is orthogonal to the longitudinal lengths of the surgical clip 100 or leg members 102, 104. Accordingly, the term "length" refers to a dimension of the surgical clip 100 and/or one or more components along its longitudinal direction. The term "height" or "vertical" refers to a dimension of the surgical clip 100 and/or one or more components along a compression axis of the leg members 102, 104. The term "thickness" refers to the dimension between opposing edges of the surgical clip 100 and/or one or more components along the compression or vertical axis. The term "width" refers to a dimension of the surgical clip 100 and/or one or more components in a lateral direction substantially transverse to the length and the height. The term "concave" and "convex" refers to the curvature of a surface or component visible when viewing an exterior of the surface or component. Similar terminology is used throughout the written disclosure.

The first and second leg members 102, 104 may include surfaces having curved portions. For example, the first leg member 102 may include a first inner surface 108 and a first outer surface 110, and the second leg member 104 may include a second inner surface 112 and a second outer surface 114. As shown in FIG. 1, the first inner surface 108 may have a concave curvature, and the first outer surface 110 may have a convex curvature. The second inner surface 112 may have a convex curvature, and the second outer surface 114 may have one or more of at least one convex curvature and/or at least one concave curvature. The concave curvature of the first inner surface 108 and/or the convex curvature of the first outer surface 110 may extend substantially the entire length of the first leg member 102. The convex curvature of the second inner surface 112 may extend substantially the entire length of the second leg member 104. The first and second inner surfaces 108, 112 may be approximated or contact in a closed configuration. The first and second inner surfaces 108, 112 may also be substantially smooth. The first leg member 102 may also include opposing side surfaces 138, 140, and the second leg member 104 may include opposing side surfaces 142, 144.

The second leg member 104 may include an inner portion 162 (e.g., an inner rib) and an outer portion 164 (e.g., an outer rib) integrally joined at a first portion 166 and a second portion 168. The inner portion 162 may have a convex inner surface 170 and a concave outer surface 172. At least one of the inner portion 162 and the outer portion 164 may have a thickness less than a thickness of the first leg member 102. The smaller thickness of the inner portion 162 and/or outer portion 164 may provide more flexibility relative to the second leg member 104 than the first leg member 102. In some embodiments, the inner portion 162 may have a greater thickness than the outer portion 164, and/or the outer portion 164 may have a greater length than the inner portion 162. The inner surface 170 of the inner portion 162 may form at least a portion of second inner surface 112, and the outer surface of the outer portion 164 may form at least a portion of first outer surface 114 of the surgical clip 100.

The inner portion 162 may be configured to resiliently deflect in the vertical, compression direction along at least a portion of its length to properly distribute pressure to tissue of varying shapes, sizes, locations and/or stiffnesses. The inner portion 162 may, additionally or alternatively, deflect along any portion of its length based on the positioning of the tissue. For example, if tissue is positioned proximate to the hinge portion 106, a proximal portion of the inner portion 162 may deflect to accommodate the tissue. However, if the tissue is positioned proximate to a latching mechanism, a distal portion of the inner portion 162 may deflect. In that sense, the surgical clip 100 may reduce stress localization due to proximity of the tissue to either of the latching mechanism and/or the hinge portion 106. The resilient compression of the inner portion 162 may also provide continuous ligating pressure to tissue in a closed and/or latched configuration, even as the tissue necrotizes and shrinks.

The inner portion 162 and the outer portion 164 may be separated by at least one transverse aperture or channel 178 extending between side surfaces 142, 144 of the second leg member 104 to enable compression of second leg member 104. For example, the channel 178 may enable the inner portion 162 to resiliently compress toward the outer portion 164 and distribute load along the length of the tissue, while more effectively gripping and retaining the tissue within the surgical clip 100. The channel 178 may also allow the outer portion 164 to have a longer length to reduce constraint on the deflection of the inner portion 162. For example, the increased length of the outer portion 164 may reduce constraint of the flexibility of the inner portion 162 as the inner portion 162 flexes and flattens during closing and/or latching. In some embodiments, the inner portion 162, the outer portion 164, and/or the channel 178 may extend greater than half of a quarter of a length of the second leg member 104. In some embodiments, the inner portion 162, the outer portion 164, and/or the channel 178 may extend greater than half of a half of a length of the second leg member 104. In some embodiments, the inner portion 162, the outer portion 164, and/or the channel 178 may extend substantially the entire length of first leg member 102.

The inner portion 162 and the outer portion 164 may have different radii of curvature between adjacent corresponding points along the length of the inner and outer portions 162, 164. In some embodiments, a first radius of of curvature of the inner portion 162 and a second radius of curvature of the outer portion 164 between adjacent corresponding points may be different for at least half of the length of the inner and outer portions 162, 164. In some embodiments, the first radius of curvature and the second radius of curvature may be different for substantially the entire length of the inner and outer portions 162, 164. The inner portion 162 may have a substantially continuous radius of curvature without any points of inflection, and the outer portion 164 may have a variable radius of curvature with at least one point of inflection. The variable radius of curvature of the outer portion may provide a variable height and vertical stability when positioned in a feeding channel 12 of a surgical clip applier 10 as illustrated in FIG. 5. For example, a proximal portion 174 of the outer portion 164 may have a greater height than a distal portion 176 of the outer portion 164. In some embodiments, the proximal portion 174 may include a convex outer surface and a concave inner surface, and the distal portion 176 may include a concave outer surface and a convex inner surface. The concave outer surface of the distal portion 176 may provide a smooth transition with the distal portion 104B to reduce irregular stress concentrations. The convex outer surface of the proximal portion 174 may project vertically to provide a contact point with walls 14, 16 of the feeding channel 12 and reduce vertical movement of the proximal end of the surgical clip 100 relative to the clip applier 10. Additional contact points may include the outer surface 110 of the first leg member 102, the bosses 146, 148, and 150 of the first leg member 102, and/or the bosses 152, 154 of the second leg member 104. The increased vertical stability of the surgical clip 100 may eliminate the need for a stability finger on a pusher member of the clip applier 10 and/or proper loading of the surgical clip 100 into jaws of the clip applier 10.

The channel 178 may also provide an anchoring point for an elongated member, such as a suture. For example, a surgeon may apply the surgical clip 100 to a tissue (e.g., a blood vessel), pass or loop the suture through the channel 178, and pass the suture through another place in the same or a different tissue to secure the clip in place. The suture passed through the channel 178 may, additionally or alternatively, secure the tissue near another location and/or approximate two tissues together.

The hinge portion 106 may be resiliently flexible and integral to the first and second leg members 102, 104. The hinge portion 106 may have a concave inner surface 116 and a convex outer surface 118. The concave inner surface 116 of the hinge portion 106 may join the first inner surface 108 of the first leg member 102 and the second inner surface 112 of the second leg member 104. The convex outer surface 118 of the hinge portion 106 may join the first outer surface 110 of the first leg member 102 and the second outer surface 114 of the second leg member 104. The hinge portion 106 may also include a curved slot 120 located between the hinge surfaces 116, 118, and may be positioned closer to the concave inner surface 116 than to the convex outer surface 118. The curved slot 120 may extend completely through the hinge portion 106 from side to side and its opposite ends may extend into the proximal end portions 102A, 102B of first and second leg members 102, 104, respectively. The curved slot 120 may provide added flexibility and resiliency to the hinge portion 106, but the concave inner surface 116 may prevent any portion of a clamped vessel from being trapped within curved slot 120.

The surgical clip 100 may also include a latching mechanism having one or more latching elements. For example, the first leg member 102 may transition to a hook portion 126 at its distal end portion 102B, and the second leg member 104 may transition to a complementary grooved and pointed tip portion 128 at its distal end portion 104B. A distal end portion of the hook portion 126 may curve inwardly and point generally toward the concave inner surface 116 of the hinge portion 106. The hook portion 126 may have one or more transverse beveled surfaces 130 and a concave inner surface which merges with the first inner surface 108 to define a latching recess 132. The tip portion 128 may be V-shaped defining a slot configured to receive the beveled surfaces 130, as the hook portion 126 deflects around the tip portion 128. The hook portion 126 and the tip portion 128 may engage to form the latching mechanism. For example, the latching recess 132 may engage with the tip portion 128 in the course of compressing the surgical clip 100 into the closed configuration (e.g., FIG. 6) that may be secured position around a vessel or other tissue.

The leg members 102, 104 may include one or more bosses along the length to engage jaws of the clip applier 10. For example, the first leg member 102 may include bosses 146, 148 protruding perpendicular to each of opposing side surfaces 138, 140 adjacent to the distal end portion 102B of the first leg member 102 and immediately inward of the hook portion 126. In the illustrated example of the surgical clip 100, the bosses 146, 148 may be cylindrical and project outwardly beyond the first outer surface 110 of first leg member 102. The bosses 146, 148 may also be coupled together by a bridge section 150. The second leg member 104 may also include bosses 152, 154 at the distal end portion 104B. The bosses 152, 154 may be cylindrical and protrude perpendicular to each of opposing side surfaces 142, 144 of the second leg member 104, extending longitudinally forward beyond the point of tip portion 128. The jaws of the clip applier 10 may engage the bosses 146, 148, 150, 152, 154 and pivot the leg members 102, 104 about the hinge portion 106 to compress the surgical clip 100 into a closed and/or latched configuration around a vessel.

As further shown in the embodiment of FIGS. 1-6, the surgical clip 100 may include at least one first tooth 134 positioned on the first leg member 102, and at least one second tooth 136 positioned on the second leg member 104. The teeth 134, 136 may be substantially rigid, such that the teeth 134, 136 do not substantially deflect when engaging tissue. The teeth 134, 136 may be positioned out-board relative to the surgical clip 100. As used herein, the term "out-board" shall refer to the positioning of the teeth 134, 136 on one or more exterior side surfaces of the surgical clip 100. For example, the teeth 134, 136 may be attached to and extend from one of the side surfaces 138-144 and laterally of the one or more of the inner surfaces 108, 112. For example, the teeth 134, 136 may extend substantially parallel to at least one of the side surfaces 138-144 and/or substantially perpendicular to at least one of the inner surfaces 108, 112. Therefore, the teeth 134, 136 may be positioned to clear the opposing inner surface 108, 112 and along a side surface 138-144 of the opposing leg member 102, 104 to enable the surgical clip 100 to close with minimal or no gap between the inner surfaces 108, 112 ensuring effective closure of small vessels. The inner surfaces 108, 112 may have no teeth and comprise a substantially smooth surface extending from the proximal ends 102A, 104B to the distal end portions 102B, 104B of the leg members 102, 104. The teeth 134, 136 may be positioned on one or both sides of at least one of the inner surfaces 108, 112 of the leg members 102, 104. The out-board teeth 134, 136 may be larger and more effective in tissue interaction. For example, the larger size of the teeth 134, 136 may be improve tissue retention and prevent the tissue from slipping out of the surgical clip. The teeth 134, 136 may be sufficiently spaced apart and not pinch tissue between adjacent teeth 134, 136. The teeth 134, 136 may further be easy to mold and not interfere with clip appliers. The teeth 134, 136 may have a variety of configurations, as discussed herein.

As depicted in FIGS. 1-6, the teeth 134, 136 may include a convex distal portion 180 and a concave proximal portion 182 (e.g., a cut-out). The concave portion 182 may extend about 90° of a proximal surface of the teeth 134, 136. The concave portion 182 may be configured to receive the tissue and prevent the tissue from slipping distally out of the surgical clip 100. The convex portion 180 and the concave portion 182 may reduce trauma to tissue compressed by the surgical clip 100. It is contemplated that the convex portion of the teeth 134, 136 may have any number of shapes, including round, disk-shaped, circular, spherical, oval, elliptical, bulbous, ring-shaped, and/or torus. It is also contemplated that the concave portion may be any number of shapes, including round, circular, spherical, oval, elliptical, U-shaped, L-shaped, and/or V-shaped. The teeth 134, 136 may further include substantially flat side surfaces on one or both sides of the teeth 134, 136. The substantially flat side surfaces 184 may facilitate approximation or contact of inner surfaces 108, 112 and reduce trauma to adjacent tissue.

Figure 6:
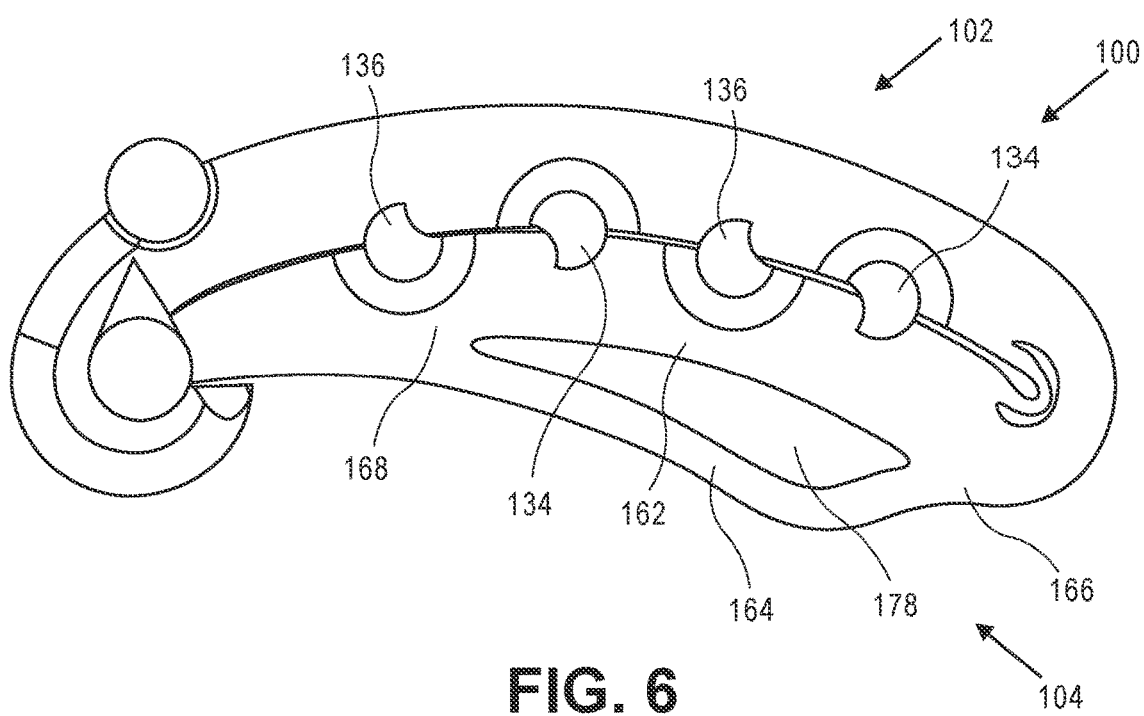
FIG. 6 illustrates a side view of an exemplary closed configuration of the first exemplary embodiment of the surgical clip of FIGS. 1-5.

As depicted in FIG. 6, the surgical clip 100 may be configured to close with minimal or no gap between the first inner surface 108 and the second inner surface 112. For example, as the surgical clip 100 closes, the first teeth 134 may extend beyond the second inner surface 112 and along at least one of the side surfaces 142, 144, and the second teeth 134 may extend beyond the first inner surface 108 and along at least one of the side surfaces 138, 140. Therefore, the teeth 134, 136 may clear the respective inner surfaces 108, 112, such that tissue may be directly compressed by the inner surfaces 108, 112 without being obstructed by the teeth 134, 136. When the teeth 134, 136 are positioned on the same side of the surgical clip 100, the teeth 134, 136 may be staggered to reduce interference. The closed and/or latched configuration may enhance compression of smaller tissue of smaller vessels, while the inner surface 112 of the second leg member 104 may resiliently deflect to accommodate the vascular tissue.

The surgical clip 100 may further be configured to clinch a suture, for example, during a partial nephrectomy. A surgeon may pass the suture with a needle through a portion of the tissue, for example, a portion of the kidney to shut off a top/bottom half of the kidney. The surgeon may close the surgical clip 100 on the suture and slide the surgical clip 100 against the tissue. The surgeon may then continue to suture the tissue without the suture pulling through the tissue or having to create a retention knot. The teeth 134, 136 may be configured to retain the suture in the middle of the surgical clip 100 without the suture sliding longitudinally toward the proximal end portion 100A or the distal end portion 100B where there may be reduced clamping pressure. The suture retention may be increased by the increased size of the teeth 134, 136.

FIGS. 1-6 illustrate the teeth 134, 136 being positioned on both sides of the first and second leg members 102, 104. For example, the surgical clip 100 may include two large teeth 134, 136 on each side of the first and second leg members, as illustrated in FIGS. 1-6. However, other numbers and configuration of the teeth 134, 136 are contemplated. The teeth 134, 136 may be positioned only on one side of at least one of the leg members 102, 104. For example, the teeth 134, 136 may be positioned only on the same side of each of the leg members 102, 104 (e.g., as illustrated in FIGS. 7-10) or only on opposite as the leg members 102, 104 (e.g., as illustrated in FIG. 11). In some embodiments, the teeth may be positioned on only one of the leg members 102, 104. For example, the first leg member 102 may include the first teeth 134 (as illustrated in FIGS. 1-6), and the second leg member 104 may have no teeth. In another example, the first leg member 102 may have no teeth, and the second leg member may include the second teeth 136 (as illustrated in FIGS. 1-6). In each of the above examples, the teeth 134, 136 may alternate side surfaces of the respectively leg member 102, 104, as further illustrated in FIGS. 1-6. It is further contemplated that the teeth 134, 136 may have different configurations, such as illustrated one or more of FIGS. 12-20.

FIGS. 7-10 illustrate a second embodiment of a surgical clip 200 of the present invention. The surgical clip 200 may have features similar to the surgical clip 100, and may be similarly represented in FIGS. 7-10. For the sake of brevity, features similar to surgical clip 100 may not be discussed with reference to the surgical clip 300.

Figures 7, 8:
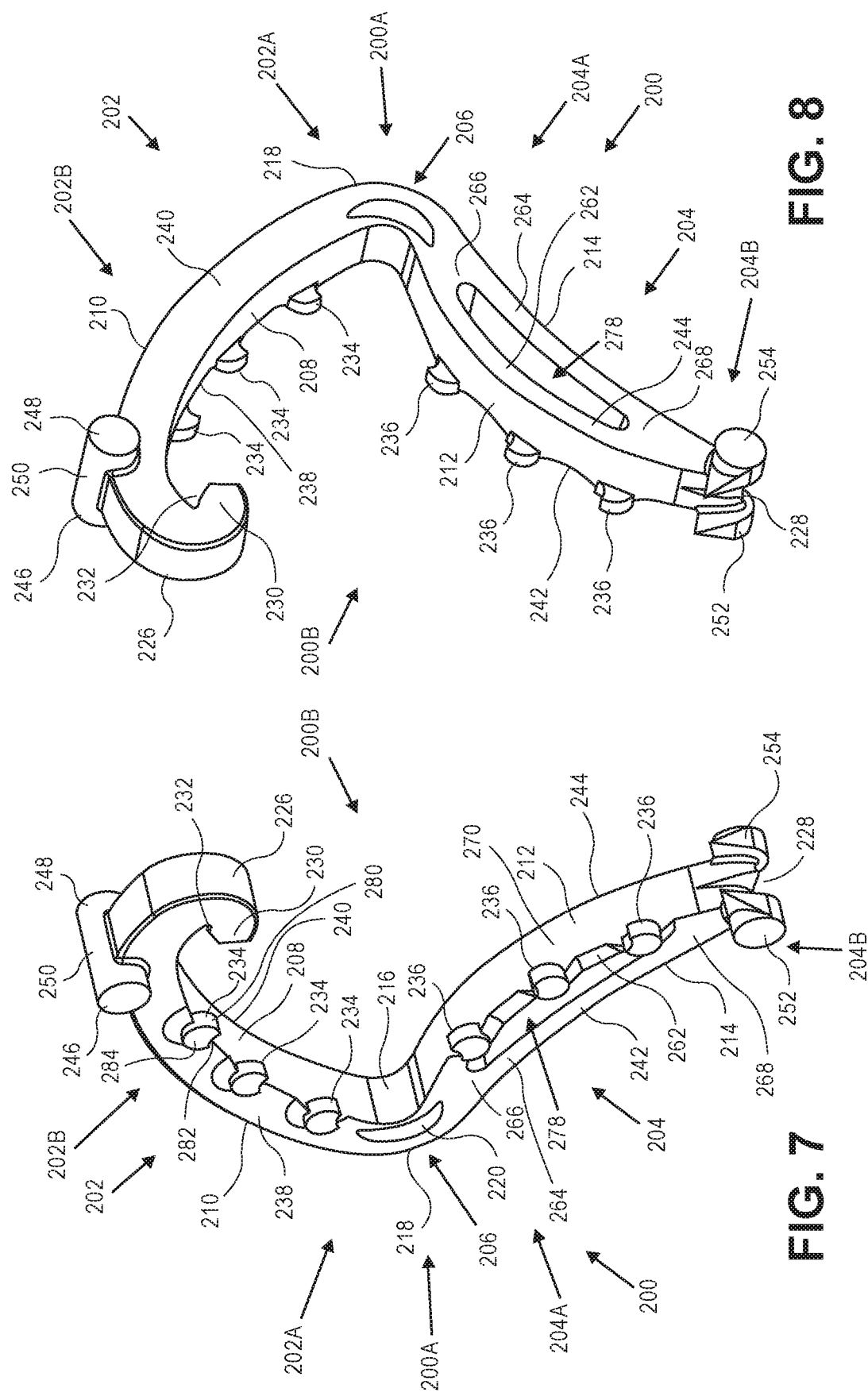
FIG. 7 illustrates a first perspective view of a second exemplary embodiment of a surgical clip of the present invention.
FIG. 8 illustrates a second perspective view of the second exemplary embodiment of the surgical clip of FIG. 7.

As illustrated, the surgical clip 200 may include a first leg member 202 and a second leg member 204 connected by a hinge portion 206. The first and second leg members 202, 204 may include surfaces having curved portions. For example, the first leg member 202 may include a first inner surface 208 and a first outer surface 210, and the second leg member 204 may include a second inner surface 212 and a second outer surface 214. As shown in FIG. 7, the first inner surface 208 may have a concave curvature, and the first outer surface 210 may have a convex curvature. The second inner surface 212 may have a convex curvature, and the second outer surface 214 may have a concave curvature. The concave curvature of the first inner surface 208 and/or the convex curvature of the first outer surface 210 may extend substantially the entire length of the first leg member 202. The convex curvature of the second inner surface 212 and/or the concave curvature of the second outer surface 214 may extend substantially the entire length of the second leg member 204. The first and second inner surfaces 208, 212 may be approximated or contact in a closed configuration. The first and second inner surfaces 208, 212 may be substantially smooth. The first leg member 202 may also include opposing side surfaces 238, 240, and the second leg member 204 may include opposing side surfaces 242, 244.

As illustrated in FIGS. 7-10, the second leg member 204 may include an inner portion 262 (e.g., an inner rib) and an outer portion 264 (e.g., an outer rib) integrally joined at a first portion 266 and a second portion 268. The inner portion 262 may include a convex inner surface 270 and a concave outer surface 272. The outer portion 264 may include a convex inner surface 274 and a concave outer surface 276. The inner portion 262 and the outer portion 264 may have different radii of curvature between adjacent corresponding points of the inner and outer portions 262, 264. In some embodiments, a first radius of curvature of the inner portion 262 and a second radius of curvature of the outer portion 264 may be different for at least half of the lengths of the inner and outer portions 262, 264. In some embodiments, the first radius of curvature and the second radius of curvature may be different for substantially the entire length of the inner and outer portions 262, 264. The inner portion 262 may have a smaller radius curvature than the outer portion, making the inner portion 262 more convex. In some embodiments, the inner portion 262 may have a smaller radius of curvature than the first leg member 202, such that the inner portion 262 may compress in a closed and/or latched configuration even in the absence of tissue. The inner portion 262 and/or the outer portion 264 may have a thickness less than a thickness of the first leg member 202, providing an increased flexibility and/or compressibility of the second leg member 204. The inner portion 262 and the outer portion 264 may be separated by at least one transverse aperture or channel 278, as discussed herein. The surgical clip 200 may be configured to anchor and/or clinch a suture, as further discussed above.

The first and second leg members 202, 204 may be integrally joined at proximal end portions 202A, 202B by a hinge portion 206. The surgical clip 200 may also include a latching mechanism having one or more latching elements. For example, the first leg member 202 may transition to a hook portion 226 at its distal end portion 202B, and the second leg member 204 may transition to a complementary grooved and pointed tip portion 228 at its distal end portion 204B. The leg members 202, 204 may further include one or more bosses along the length to engage jaws of the clip applier 10. For example, the first leg member 202 may include bosses 246, 248 protruding perpendicular to each of opposing side surfaces 238, 240, and the second leg member 204 bosses 252, 254 protruding perpendicular to each of the opposing sides surfaces 242, 244. The bosses 246, 248 of the first leg member 202 may be coupled together by a bridge section 250.

As further illustrated in FIGS. 7-10, the surgical clip 200 may also include at least one first tooth 234 attached to a side of the first leg member 202 and at least one second tooth 236 attached to the same side of the second leg member 204. For example, the first teeth 234 may be attached to and extend from a side surface 238, and the second teeth 236 may be attached to and extend from a side surface 242 substantially parallel to the side surface 238. Accordingly, the first teeth 234 and the second teeth 236 may be positioned on the same side of the surgical clip 200 (e.g., side surfaces 238, 242), and the opposite side of the surgical clip 200 may be free of teeth (e.g., side surfaces 240, 244). Positioning the teeth 234, 236 on the same side of the surgical clip 200 may reduce trauma induced on more sensitive tissue. The teeth 234, 236 may be positioned out-board similar to the surgical clip 100 and/or closed with minimal or no gap between the inner surfaces 208, 212, as discussed above. The teeth 234, 236 may also have any number of shapes, as further discussed above.

In some embodiments, the teeth may be positioned on only one of the leg members 202, 204. For example, first leg member 202 may include the first teeth 234 (as illustrated in FIGS. 7-10), and the second leg member 204 may have no teeth. In another example, the first leg member 202 may have no teeth, and the second leg member may include the second teeth 236 (as illustrated in FIGS. 7-10). In each of the above examples, the teeth 234, 236 may alternate side surfaces of the respectively leg member 202, 204.

FIG. 11 illustrates a third embodiment of a surgical clip 300 of the present invention. The surgical clip 300 may have features similar to at least one of surgical clips 100, 200, and may be similarly represented in FIG. 11. For the sake of brevity, features similar to at least one of surgical clips 100, 200 may not be discussed with reference to the surgical clip 300.

As illustrated, the surgical clip 300 may include a first leg member 302 and a second leg member 304 connected by a hinge portion 306. The first and second leg members 302, 304 may include surfaces having curved portions. For example, the first leg member 302 may include a first inner surface 308 and a first outer surface 310, and the second leg member 304 may include a second inner surface 312 and a second outer surface 314. The first inner surface 308 may have a concave curvature, and the first outer surface 310 may have a convex curvature. The second inner surface 312 may have a convex curvature, and the second outer surface 314 may have a concave curvature. The concave curvature of the first inner surface 308 and/or the convex curvature of the first outer surface 310 may extend substantially the entire length of the first leg member 302. The convex curvature of the second inner surface 312 and/or the concave curvature of the second outer surface 314 may extend substantially the entire length of the second leg member 304. The first and second inner surfaces 308, 312 may be approximated or contact in a closed configuration. The first and second inner surfaces 308, 312 may be substantially smooth. The first leg member 302 may also include opposing side surfaces 338, 340, and the second leg member 304 may include opposing side surfaces 342, 344.

The second leg member 304 may include an inner portion 362 (e.g., an inner rib) and an outer portion 364 (e.g., an outer rib) integrally joined at a first portion 366 and a second portion 368. The inner portion 362 may have a convex inner surface and a concave outer surface. The outer portion 364 may have a convex inner surface and a concave outer surface. The inner portion 362 and the outer portion 364 may have a different radii of curvature between adjacent corresponding points along the length of the inner and outer portions 362, 364. In some embodiments, a first radius of curvature of the inner portion 362 and a second radius of curvature of the outer portion 364 may be different for at least half of the lengths of the inner and outer portions 362, 364. In some embodiments, the first radius of curvature and the second radius of curvature may be different for substantially the entire length of the inner and outer portions 362, 364. The inner portion 362 may have a smaller radius curvature than the outer portion, making the inner portion 362 more convex. In some embodiments, the inner portion 362 may have a smaller radius of curvature than the first leg member 302, such that the inner portion 362 may compress in a closed and/or latched configuration even in the absence of tissue. The inner portion 362 and/or the outer portion 364 may have a thickness less than a thickness of the first leg member 302, providing an increased flexibility and/or compressibility of the second leg member 304. The inner portion 362 and the outer portion 364 may be separated by at least one transverse aperture or channel 378, as discussed above. The surgical clip 300 may be configured to anchor and/or clinch a suture, as further discussed above.

The surgical clip 300 may also include a latching mechanism having one or more latching elements. For example, the first leg member 302 may transition to a hook portion 326 at its distal end portion 302B, and the second leg member 304 may transition to a complementary grooved and pointed tip portion 328 at its distal end portion 304B. The leg members 302, 304 may further include one or more bosses along the length to engage jaws of the clip applier 10. For example, the first leg member 302 may include bosses 346, 348 protruding perpendicular to each of opposing side surfaces 338, 340, and the second leg member 304 bosses 352, 354 protruding perpendicular to each of the opposing sides 342, 344. The bosses 346, 348 of the first leg member 302 may be coupled together by a bridge section 350.

As further illustrated in FIG. 11, the surgical clip 300 may include at least one first tooth 334 positioned on a first side the first leg member 302 and at least one second tooth 336 positioned on a second side of the second leg member 304 opposite of the first side. For example, the first teeth 334 may extend from a side surface 338, and the second teeth 336 may extend from a side surface 344. Accordingly, the teeth 334, 336 may be positioned on opposite sides of the surgical clip 300, and a side surface 340 of the first leg member 302 and a side surface 342 of the second leg member 304 may have no teeth. Positioning the teeth 334, 336 on opposite sides of the surgical clip 300 may enhance engagement of the tissue while reducing the number of teeth and resultant tissue trauma. The teeth 234, 236 may be positioned out-board similar to the surgical clip 100, as discussed above. The teeth 234, 236 may also have any number of shapes, as further discussed above.

FIG. 12 illustrates a fourth embodiment of a surgical clip 400 of the present invention. The surgical clip 400 may include one or more features similar to at least one of surgical clips 100-300, and may be similarly represented in FIG. 12. For the sake of brevity, features similar to those of at least one of surgical clips 100-300 may not be discussed with reference to the surgical clip 400.

The surgical clip 400 may include a first leg member 402 and a second leg member 404 connected by a hinge portion 406. The first and second leg members 402, 404 may include surfaces having curved portions. For example, the first leg member 402 may include a first inner surface 408 and a first outer surface 410, and the second leg member 404 may include a second inner surface 412 and a second outer surface 414. The first inner surface 408 may have a concave curvature, and the first outer surface 410 may have a convex curvature. The second inner surface 412 may have a convex curvature, and the second outer surface 414 may have a concave curvature. The concave curvature of the first inner surface 408 and/or the convex curvature of the first outer surface 410 may extend substantially the entire length of the first leg member 402. The convex curvature of the second inner surface 412 and/or the concave curvature of the second outer surface 414 may extend substantially the entire length of the second leg member 404. The first and second inner surfaces 408, 412 may be approximated or contact in a closed configuration. The first and second inner surfaces 408, 412 may be substantially smooth. The first leg member 402 may also include opposing side surfaces 438, 440, and the second leg member 404 may include opposing side surfaces 442, 444.

The second leg member 404 may include an inner portion 462 (e.g., an inner rib) and an outer portion 464 (e.g., an outer rib) integrally joined at a first portion 466 and a second portion 468. The inner portion 462 may have a convex inner surface and a concave outer surface. The outer portion 464 may have a convex inner surface and a concave outer surface. The inner portion 462 and the outer portion 464 may have different radii of curvature between adjacent corresponding points along the length of the inner and outer portions 462, 464. In some embodiments, a first radius of curvature of the inner portion 462 and a second radius of curvature of the outer portion 464 may be different for at least half of the lengths of the inner and outer portions 462, 464. In some embodiments, the first radius of curvature and the second radius of curvature may be different for substantially the entire length of the inner and outer portions 462, 464. The inner portion 462 may have a smaller radius curvature than the outer portion 464, making the inner portion 462 more convex. In some embodiments, the inner portion 462 may have a smaller radius of curvature than the first leg member 402, such that the inner portion 462 may compress in a closed and/or latched configuration even in the absence of tissue. The inner portion 462 and/or the outer portion 464 may have a thickness less than a thickness of the first leg member 402, providing an increased flexibility and/or compressibility of the second leg member 404. The inner portion 462 and the outer portion 464 may be separated by at least one transverse aperture or channel 478, as discussed above. The surgical clip 400 may be configured to anchor and/or clinch a suture, as further discussed above.

The surgical clip 400 may also include a latching mechanism having one or more latching elements. For example, the first leg member 402 may transition to a hook portion 426 at its distal end portion 402B, and the second leg member 404 may transition to a complementary grooved and pointed tip portion 428 at its distal end portion 404B. The leg members 402, 404 may further include one or more bosses along the length to engage jaws of the clip applier 10. For example, the first leg member 402 may include bosses 446, 448 protruding perpendicular to each of opposing side surfaces 438, 440, and the second leg member 404 bosses 452, 454 protruding perpendicular to each of the opposing sides 442, 444. The bosses 446, 448 of the first leg member 402 may be coupled together by a bridge section 450.

As further illustrated in FIG. 12, the surgical clip 400 may include at least one first tooth 434 and/or at least one second tooth 436 comprising convex members that provide atraumatic tissue clamping surfaces. In some embodiments, the convex members may include convex segments greater than about 180°. In some embodiments, the convex members may include convex segments greater than about 270°. In some embodiments, the convex members may include a convex segment about 360°. It is contemplated that the one or more convex members may be any number of shapes, including round, circular, disk-shaped, spherical, oval, elliptical, bulbous, ring-shaped, and/or torus.

As further illustrated in FIG. 12, the first teeth 434 may extend from a first side surface 438 of the first leg member 402 laterally of a first inner surface 408, and the one or more second teeth 435 may extend from a second side surface 442 of the second leg member 404 laterally of a second inner surface 512. The sides 438, 442 may be on the same side of the leg members 402, 404. Alternatively, in some embodiments, the teeth 434, 436 may be positioned on both sides of at least one of the leg members 402, 404, e.g., as illustrated in FIGS. 1-6. In some embodiments, the teeth 434, 436 may be positioned only on opposite sides of the leg members 402, 404, e.g., as illustrated in FIG. 11. The circular configuration of the teeth 434, 436 may even further reduce trauma to tissue. The teeth 434, 436 may be positioned out-board similar to the surgical clip 100, as discussed above.

In some embodiments, the teeth may be positioned on only one of the leg members 402, 404. For example, the first leg member 402 may include the first teeth 434, and the second leg member 404 may have no teeth. In another example, the first leg member 402 may have no teeth, and the second leg member 404 may include the second teeth 436. In each of the above examples, the teeth 434, 436 may alternate side surfaces of the respectively leg member 402, 404 as discussed above.

Figures 13, 14:
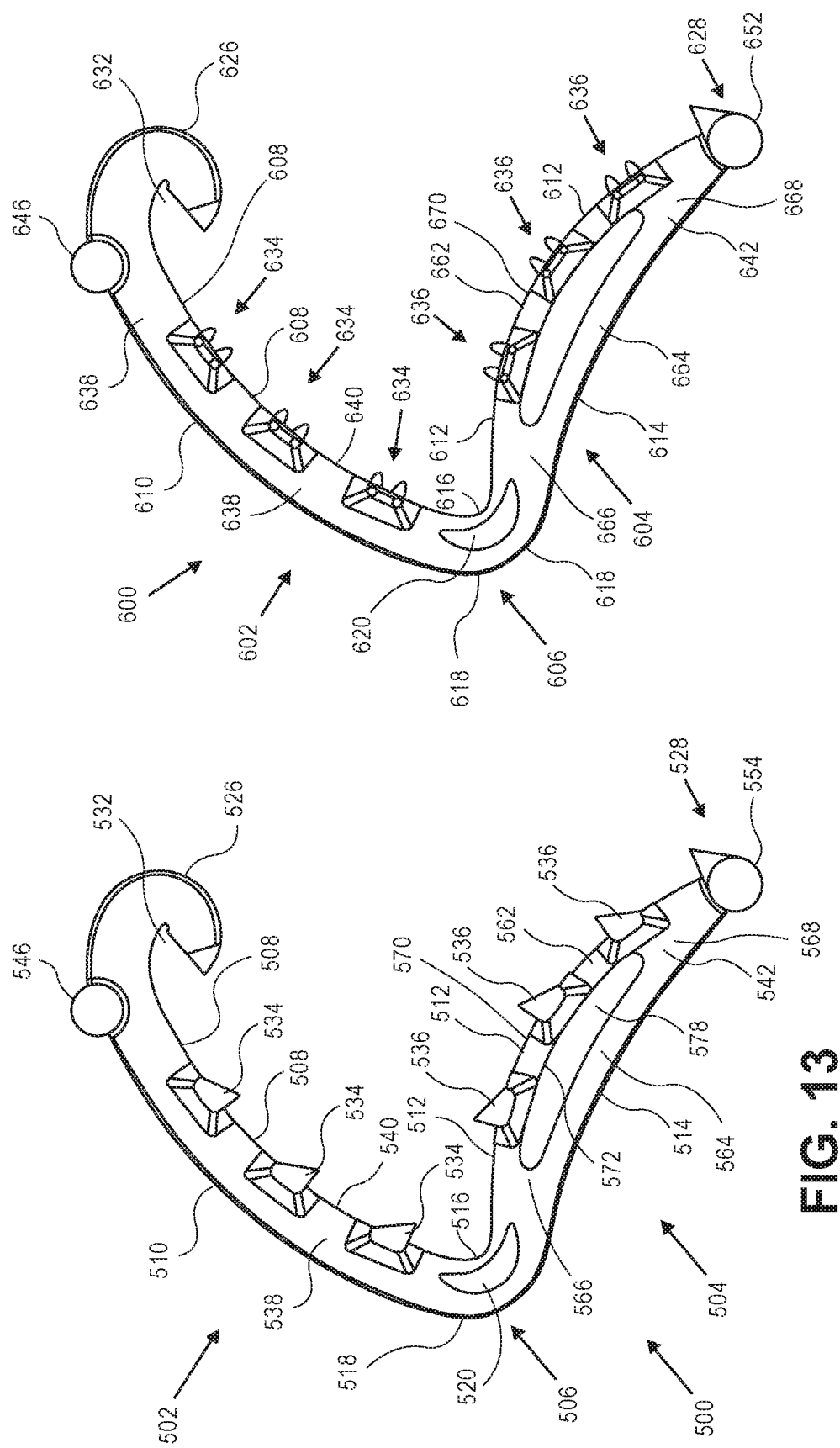
FIG. 13 illustrates a perspective view of a fifth exemplary embodiment of the surgical clip of the present invention.
FIG. 14 illustrates a perspective view of a sixth exemplary embodiment of the surgical clip of the present invention.

FIG. 13 illustrates a fifth embodiment of a surgical clip 500 of the present invention. The surgical clip 500 may include one or more features similar to at least one of surgical clips 100-400, and may be similarly represented in FIG. 13. For the sake of brevity, features similar to those of at least one of surgical clips 100-400 may not be discussed with reference to the surgical clip 500.

The surgical clip 500 may include a first leg member 502 and a second leg member 504 connected by a hinge portion 506. The first and second leg members 502, 504 may include surfaces having curved portions. For example, the first leg member 502 may include a first inner surface 508 and a first outer surface 510, and the second leg member 504 may include a second inner surface 512 and a second outer surface 514. The first inner surface 508 may have a concave curvature, and the first outer surface 510 may have a convex curvature. The second inner surface 512 may have a convex curvature, and the second outer surface 514 may have a concave curvature. The concave curvature of the first inner surface 508 and/or the convex curvature of the first outer surface 510 may extend substantially the entire length of the first leg member 502. The convex curvature of the second inner surface 512 and/or the concave curvature of the second outer surface 514 may extend substantially the entire length of the second leg member 504. The first and second inner surfaces 508, 512 may be approximated or contact in a closed configuration. The first and second inner surfaces 508, 512 may be substantially smooth. The first leg member 502 may also include opposing side surfaces 538, 540, and the second leg member 504 may include opposing side surfaces 542, 544.

The second leg member 504 may include an inner portion 562 (e.g., an inner rib) and an outer portion 564 (e.g., an outer rib) integrally joined at a first portion 566 and a second portion 568. The inner portion 562 may have a convex inner surface 570 and a concave outer surface 572. The outer portion 564 may have a convex inner surface and a concave outer surface. The inner portion 562 and the outer portion 564 may have different radii of curvature between adjacent corresponding points along the length of the inner and outer portions 562, 564. In some embodiments, a first radius of curvature of the inner portion 562 and a second radius of curvature of the outer portion 564 may be different for at least half of the lengths of the inner and outer portions 562, 564. In some embodiments, the first radius of curvature and the second radius of curvature may be different for substantially the entire length of the inner and outer portions 562, 564. The inner portion 562 may have a smaller radius curvature than the outer portion, making the inner portion 562 more convex. In some embodiments, the inner portion 562 may have a smaller radius of curvature than the first leg member 502, such that the inner portion 562 may compress in a closed and/or latched configuration even in the absence of tissue. The inner portion 562 and/or the outer portion 564 may have a thickness less than a thickness of the first leg member 502, providing an increased flexibility and/or compressibility of the second leg member 504. The inner portion 562 and the outer portion 564 may be separated by at least one transverse aperture or channel 578, as discussed above. The surgical clip 500 may be configured to anchor and/or clinch a suture, as further discussed above.

The surgical clip 500 may also include a latching mechanism having one or more latching elements. For example, the first leg member 502 may transition to a hook portion 526 at its distal end portion 502B, and the second leg member 504 may transition to a complementary grooved and pointed tip portion 528 at its distal end portion 504B. The leg members 502, 504 may further include one or more bosses along the length to engage jaws of the clip applier 10. For example, the first leg member 502 may include bosses 546, 548 protruding perpendicular to each of opposing side surfaces 538, 540, and the second leg member 504 bosses 552, 554 protruding perpendicular to each of the opposing sides 542, 544. The bosses 546, 548 of the first leg member 502 may be coupled together by a bridge section 550.

As further illustrated, the surgical clip 500 may include at least one first tooth 534 and/or at least one second teeth 536. One or more of the teeth 534, 536 may comprise proximally angled protrusions. The proximally angled protrusions may improve tissue retention and prevent the tissue form sliding out of the clip 500 distally (e.g., a "watermelon-seeding" effect) when the surgical clip 500 is closed. The tips of the protrusions may be relatively sharp or rounded to reduce trauma to tissue.

As further discussed above, the first teeth 534 may extend from a first side surface 538 of the first leg member 502 laterally of a first inner surface 508, and the one or more second teeth 535 may extend from a second side surface 544 of the second leg member 504 laterally of a second inner surface 512. In some embodiments, the teeth 534, 536 may be positioned on both sides of at least one of the leg members 502, 504, e.g., as illustrated in FIGS. 1-6. In some embodiments, the teeth 534, 536 may be positioned only on the same side of the leg members 502, 504, e.g., as illustrated in FIGS. 7-10. In some embodiments, the teeth 534, 536 may be positioned only on opposite sides of the leg members 502, 504, as illustrated in FIG. 11. The teeth 534, 536 may be positioned out-board similar to the surgical clip 100, as discussed above.

In some embodiments, the teeth may be positioned on only one of the leg members 502, 504. For example, the first leg member 502 may include the first teeth 534, and the second leg member 504 may have no teeth. In another example, the first leg member 502 may have no teeth, and the second leg member 504 may include the second teeth 536. In each of the above examples, the teeth 534, 536 may alternate side surfaces of the respectively leg member 502, 504 as discussed above.

FIG. 14 illustrates a sixth embodiment of a surgical clip 600 of the present invention. The surgical clip 600 may include one or more features similar to at least one of surgical clips 100-500, and may be similarly represented in FIG. 13. For the sake of brevity, features similar to those of at least one of surgical clips 100-500 may not be discussed with reference to the surgical clip 600.

The surgical clip 600 may include a first leg member 602 and a second leg member 604 connected by a hinge portion 606. The first and second leg members 602, 604 may include surfaces having curved portions. For example, the first leg member 602 may include a first inner surface 608 and a first outer surface 610, and the second leg member 604 may include a second inner surface 612 and a second outer surface 614. The first inner surface 608 may have a concave curvature, and the first outer surface 610 may have a convex curvature. The second inner surface 612 may have a convex curvature, and the second outer surface 614 may have a concave curvature. The concave curvature of the first inner surface 608 and/or the convex curvature of the first outer surface 610 may extend substantially the entire length of the first leg member 602. The convex curvature of the second inner surface 612 and/or the concave curvature of the second outer surface 614 may extend substantially the entire length of the second leg member 604. The first and second inner surfaces 608, 612 may be approximated or contact in a closed configuration. The first and second inner surfaces 608, 612 may be substantially smooth. The first leg member 602 may also include opposing side surfaces 638, 640, and the second leg member 604 may include opposing side surfaces 642, 644.

The second leg member 604 may include an inner portion 662 (e.g., an inner rib) and an outer portion 664 (e.g., an outer rib) integrally joined at a first portion 666 and a second portion 668. The inner portion 662 may have a convex inner surface 670 and a concave outer surface. The outer portion 664 may have a convex inner surface and a concave outer surface. The inner portion 662 and outer portion 664 may have different radii of curvature between adjacent corresponding points along the lengths of the inner and outer portions 662, 664. In some embodiments, a first radius of curvature of the inner portion 662 and a second radius of curvature of the outer portion 664 may be different for at least half of the lengths of the inner and outer portions 662, 664. In some embodiments, the first radius of curvature and the second radius of curvature may be different for substantially the entire length of the inner and outer portions 662, 664. The inner portion 662 may have a smaller radius curvature than the outer portion, making the inner portion 662 more convex. In some embodiments, the inner portion 662 may have a smaller radius of curvature than the first leg member 602, such that the inner portion 662 may compress in a closed and/or latched configuration even in the absence of tissue. The inner portion 662 and/or the outer portion 664 may have a thickness less than a thickness of the first leg member 602, providing an increased flexibility and/or compressibility of the second leg member 604. The inner portion 662 and the outer portion 664 may be separated by at least one transverse aperture or channel 678, as discussed above. The surgical clip 600 may be configured to anchor and/or clinch a suture, as further discussed above.

The surgical clip 600 may also include a latching mechanism having one or more latching elements. For example, the first leg member 602 may transition to a hook portion 626 at its distal end portion 602B, and the second leg member 604 may transition to a complementary grooved and pointed tip portion 628 at its distal end portion 604B. The leg members 602, 604 may further include one or more bosses along the length to engage jaws of the clip applier 10. For example, the first leg member 602 may include bosses 646, 648 protruding perpendicular to each of opposing side surfaces 638, 640, and the second leg member 604 bosses 652, 654 protruding perpendicular to each of the opposing sides 642, 644. The bosses 646, 648 of the first leg member 602 may be coupled together by a bridge section 650.

As further illustrated in FIG. 14, the surgical clip 600 may include one or more first teeth 634 and/or one or more second teeth 636 having a plurality a prongs. As further discussed above, the first teeth 634 may extend from a first side surface 638 of the first leg member 602 laterally of a first inner surface 608, and the one or more second teeth 635 may extend from a second side surface 644 of the second leg member 604 laterally of a second inner surface 612. In some embodiments, the teeth 634, 636 may be positioned on both sides of at least one of the leg member 602, 604, e.g., as illustrated in FIGS. 1-6. In some embodiments, the teeth 634, 636 may be positioned only on the same side of the leg members 602, 604, e.g., as illustrated in FIGS. 7-10. In some embodiments, the teeth 634, 636 may be positioned only on opposite sides of the leg members 602, 604, as illustrated in FIG. 11. The teeth 634, 636 may be positioned out-board similar to the surgical clip 100, as discussed above.

In some embodiments, the teeth may be positioned on only one of the leg members 602, 604. For example, the first leg member 602 may include the first teeth 634, and the second leg member 604 may have no teeth. In another example, the first leg member 602 may have no teeth, and the second leg member 604 may include the second teeth 636. In each of the above examples, the teeth 634, 636 may alternate side surfaces of the respectively leg member 602, 604 as discussed above.

FIGS. 15 and 16 illustrate a seventh embodiment of a surgical clip 700 of the present invention. The surgical clip 700 may include one or more features similar to at least one of surgical clips 100-600, and may be similarly represented in FIGS. 15 and 16. For the sake of brevity, features similar to those of at least one of surgical clips 100-600 may not be discussed with reference to the surgical clip 700.

The surgical clip 700 may include a first leg member 702 and a second leg member 704 connected by a hinge portion 706. The first and second leg members 702, 704 may include surfaces having curved portions. For example, the first leg member 702 may include a first inner surface 708 and a first outer surface 710, and the second leg member 704 may include a second inner surface 712 and a second outer surface 714. The first inner surface 708 may have a concave curvature, and the first outer surface 710 may have a convex curvature. The second inner surface 712 may have a convex curvature, and the second outer surface 714 may have a concave curvature. The concave curvature of the first inner surface 708 and/or the convex curvature of the first outer surface 710 may extend substantially the entire length of the first leg member 702. The convex curvature of the second inner surface 712 and/or the concave curvature of the second outer surface 714 may extend substantially the entire length of the second leg member 704. The first and second inner surfaces 708, 712 may be approximated or contact in a closed configuration. The first and second inner surfaces 708, 712 may be substantially smooth. The first leg member 702 may also include opposing side surfaces 738, 740, and the second leg member 704 may include opposing side surfaces 742, 744.

The second leg member 704 may include an inner portion 762 (e.g., an inner rib) and an outer portion 764 (e.g., an outer rib) integrally joined at a first portion 766 and a second portion 768. The inner portion 762 may have a convex inner surface 770 and a concave outer surface 772. The outer portion 764 may have a convex inner surface and a concave outer surface. The inner portion 762 and outer portion 764 may have different radii of curvature between adjacent corresponding points along the length of the inner and outer portions 762, 764. In some embodiments, a first radius of curvature of the inner portion 762 and a second radius of curvature of the outer portion 764 may be different for at least half of the lengths of the inner and outer portions 762, 764. In some embodiments, the first radius of curvature and the second radius of curvature may be different for substantially the entire length of the inner and outer portions 762, 764. The inner portion 762 may have a smaller radius curvature than the outer portion, making the inner portion 762 more convex. In some embodiments, the inner portion 762 may have a smaller radius of curvature than the first leg member 602, such that the inner portion 762 may compress in a closed and/or latched configuration even in the absence of tissue. The inner portion 762 and/or the outer portion 764 may have a thickness less than a thickness of the first leg member 702, providing an increased flexibility and/or compressibility of the second leg member 704. The inner portion 762 and the outer portion 764 may be separated by at least one transverse aperture or channel 778, as discussed above. The surgical clip 700 may be configured to anchor and/or clinch a suture, as further discussed above.

The surgical clip 700 may also include a latching mechanism having one or more latching elements. For example, the first leg member 702 may transition to a hook portion 726 at its distal end portion 702B, and the second leg member 704 may transition to a complementary grooved and pointed tip portion 728 at its distal end portion 704B. The leg members 702, 704 may further include one or more bosses along the length to engage jaws of the clip applier 10. For example, the first leg member 702 may include bosses 746, 748 protruding perpendicular to each of opposing side surfaces 738, 740, and the second leg member 704 bosses 752, 754 protruding perpendicular to each of the opposing sides 742, 744. The bosses 746, 748 of the first leg member 702 may be coupled together by a bridge section 750.

As further illustrated in FIGS. 15 and 16, the first tooth 734 may be a single elongated tooth or ridge on the first leg member 702 and, in some embodiments, the first tooth 734 may extend between a proximal end portion 702A and a distal end portion 702B. The second tooth 736 may be a single elongated tooth or ridge on the second leg member 704 and, in some embodiments, the second tooth 736 may extend between a proximal end portion 704A and a distal end portion 704B. The first tooth 734 may include first and second planar side sides and an inner surface having one or grooves 738 to improve tissue retention. The teeth 734, 736 may be positioned out-board similar to the surgical clip 100, as discussed above. In some embodiments, only one of the leg members 702, 704 has teeth. For example, the first leg member 702 may include one or more first teeth 734 on side surfaces, and the second leg member 704 has no teeth. In another example, the first leg member 702 has no teeth, and the second leg member 704 may include one or more second teeth 736 on side surfaces.

FIGS. 17-20 illustrate an eighth embodiment of a surgical clip 800 of the present invention. The surgical clip 800 may include one or more features similar to at least one of surgical clips 100-700, and may be similarly represented in FIGS. 17-20. For the sake of brevity, features similar to those of at least one of surgical clips 100-700 may not be discussed with reference to the surgical clip 800.

As illustrated, the surgical clip 800 may include a first leg member 802 and a second leg member 804 connected by a hinge portion 806. The first and second leg members 802, 804 may include surfaces having curved portions. For example, the first leg member 802 may include a first inner surface 808 and a first outer surface 810, and the second leg member 804 may include a second inner surface 812 and a second outer surface 814. The first inner surface 808 may have a concave curvature, and the first outer surface 810 may have a convex curvature. The second inner surface 812 may have a convex curvature, and the second outer surface 814 may have one or more of at least one convex curvature and/or at least one concave curvature. The concave curvature of the first inner surface 808 and/or the convex curvature of the first outer surface 810 may extend substantially the entire length of the first leg member 802. The convex curvature of the second inner surface 812 may extend substantially the entire length of the second leg member 804. The first and second inner surfaces 808, 812 may be approximated or contact in a closed configuration. The first and second inner surfaces 808, 812 may be substantially smooth. The first leg member 802 may also include opposing side surfaces 838, 840, and the second leg member 804 may include opposing side surfaces 842, 844.

The second leg member 804 may include an inner portion 862 (e.g., an inner rib) and an outer portion 864 (e.g., an outer rib) integrally joined at a first portion 866 and a second portion 868. The inner portion 862 may include a convex inner surface 870 and a concave outer surface 872. The outer portion 864 may include a concave inner surface and a convex outer surface. The inner portion 862 and outer portion 864 may have different radii of curvature between adjacent corresponding points along the length of the inner and outer portions 862, 864. In some embodiments, a first radius of curvature of the inner portion 862 and a second radius of curvature of the outer portion 864 may be different for at least half of the lengths of the inner and outer portions 862, 864. In some embodiments, the first radius of curvature and the second radius of curvature may be different for substantially the entire length of the inner and outer portions 862, 864. The inner portion 862 may have a larger radius curvature than the outer portion 864, making the inner portion 862 less curved than the outer portion 864. The more curvature of the outer portion 864 may reduce constraint on the deflection of the inner portion 864 during closure and/or latching of the surgical clip 800. The outer surface 814 may have a concave curvature at the first and second portions 866, 868 where the inner portion 862 and outer portion 864 join. The inner portion 862 and/or the outer portion 864 may have a thickness less than a thickness of the first leg member 802, providing an increased flexibility and/or compressibility of the second leg member 804. The inner portion 862 and the outer portion 864 may be separated by at least one transverse aperture or channel 878, as discussed above. The surgical clip 800 may be configured to anchor and/or clinch a suture, as further discussed above.

The surgical clip 800 may also include a latching mechanism having one or more latching elements. For example, the first leg member 802 may transition to a hook portion 826 at its distal end portion 802B, and the second leg member 804 may transition to a complementary grooved and pointed tip portion 828 at its distal end portion 804B. The leg members 802, 804 may further include one or more bosses along the length to engage jaws of the clip applier 10. For example, the first leg member 802 may include bosses 846, 848 protruding perpendicular to each of opposing side surfaces 838, 840, and the second leg member 804 bosses 852, 854 protruding perpendicular to each of the opposing sides 842, 844. The bosses 846, 848 of the first leg member 802 may be coupled together by a bridge section 850.

As further illustrated in FIG. 17-20, the surgical clip 800 may include at least one tooth 836 positioned on at least one of the first leg member 802 and the second leg member 804. For example, the second leg member 804 may have at least one tooth 836 positioned on the second inner surface 812, and the first leg member may have no teeth. The at least one tooth 836 may be spaced apart and positioned on at least one lateral side of the second inner surface 812. For example, the one or more teeth 836 may have a side surface that extends continuously from or flush with one of the side surfaces 842, 844. The second leg member 804 may have a first row of at least one first tooth 836 on a first lateral side of the second inner surface 812 and a second row of at least one second tooth 836 on a second lateral side of the second inner surface 812. For example, a plurality of first teeth 836 and a plurality of second teeth 836 may alternate laterally along a length of the inner surface 812 of the second leg member 804. The at least one tooth 836 may include an inner surface substantially parallel to the second second inner surface 812 and/or substantially flat. As illustrated in FIG. 20, due to the slight curvature of the inner surface 812 along the length of the tooth 836, the tooth 836 may be substantially flat and substantially parallel to the inner surface 812 along at least a portion of the length of the first leg member 802. The at least one tooth 836 may further have first and second substantially flat side surfaces that extend substantially vertically from the inner surface of the second leg member, for example, with one of the side surfaces being flush with one of the side surfaces 842, 844. The at least one tooth 836 may also include substantially flat proximal and distal surfaces that extend at an angle from the second inner surface 812. The proximal and distal surfaces of the tooth 836 may extend at an obtuse angle from the second inner surface 812. For example, in some embodiments as illustrated in FIGS. 17-20, the proximal and distal surfaces of the tooth 836 may extend at substantially the same obtuse angle forming a longitudinally symmetrical shape of the tooth 836. Thus, the teeth 836 may be substantially atraumatic without any sharp angles and be sufficiently spaced apart, such that the surgical clip 800 would not cause unnecessary trauma to the tissue and/or pinch tissue between adjacent teeth 836.

The teeth 836 may have similar advantages as the "outboard" teeth discussed above. The teeth 836 would not impede full closure of the surgical clip, providing more effective occlusion of smaller vessels. In that sense, inner surfaces 808, 812 may be substantially smooth, and the teeth 836 may be spaced apart. The teeth 836 may also allow the teeth 836 to be larger and more effective in tissue interaction. The larger number of teeth 836 may further allow for reduced number of teeth 836. As illustrated in FIGS. 17-20, the surgical clip 800 may have two rows of three teeth 836. Thus, the teeth 836 may be easy to mold and not interfere with clip appliers. The surgical clip 800 may further provide a favorable low-profile in the vertical and lateral direction when in the closed configuration, as illustrated in FIG. 20.

The first leg member 802 may have at least one longitudinal channel 837 in one or more of the side surface 838, 840, recessed from and adjacent to the first inner surface 808, such that the longitudinal channel 837 is defined between one of the side surfaces 838, 840 and the first inner surface 808. As further illustrated in FIG. 20, the at least one longitudinal channel 837 may be configured to receive the one or more teeth 836 to approximate or contact the inner surfaces 808, 812 with minimal or no gap. In that sense, the first inner surface 808 may be substantially smooth, and the second inner surface 812 extending between the teeth 836 may be substantially smooth. For example, a first longitudinal channel 837 through the side surface 838 may receive the plurality of first teeth, and a second longitudinal channel 837 through the side surface 840 may receive the plurality of second teeth. For example, as illustrated, each of the longitudinal channels 837 may be positioned on opposite sides of the first leg member 802 and configured to receive the teeth 836 spaced in a row along the second leg member 804. Therefore, the first inner surface 808 may be disposed on the inner surface of an inner rib 860 defined by the flanking longitudinal channels 837. The inner surface of the rib 860 may be continuous with the inner surface 816 of the hinge member 806 and/or the inner surface of the hook portion 826. The first leg member 802 may have a substantially constant thickness between the inner and outer surface 808, 810 along a length including the inner rib 860 the inner rib 860 may be solid and continuously formed on the first leg member 802 without any channels or openings therethrough to facilitate manufacturing (e.g., molding) of such a small component. The inner rib 860 may extend substantially the entire length of the first leg member 802. Thus, the first and second longitudinal channels 837 may be distinct and not connected with each other. As illustrated in FIG. 20, the inner rib 860 may be received between the rows of teeth 836 in the closed configuration.

In some alternative embodiments, the one or more teeth 836 may be positioned on the first leg member 802, and the at least one longitudinal channel 837 may be positioned on the first leg member 804. In some further embodiments, each of the first and second leg members 802, 804 may include one or more teeth 836 and at least one longitudinal channel 837. For example, the first inner surface 808 may have a row of one or more teeth 836 on a first lateral side and a longitudinal channel 837 on a second lateral side, and the second inner surface 812 may comprise a longitudinal channel 837 on the first lateral side and a row of one or more teeth 836 on the second lateral side. Therefore, each of the longitudinal channels 837 may receive the one or more teeth 836 on the opposite leg member.

Figure 23:
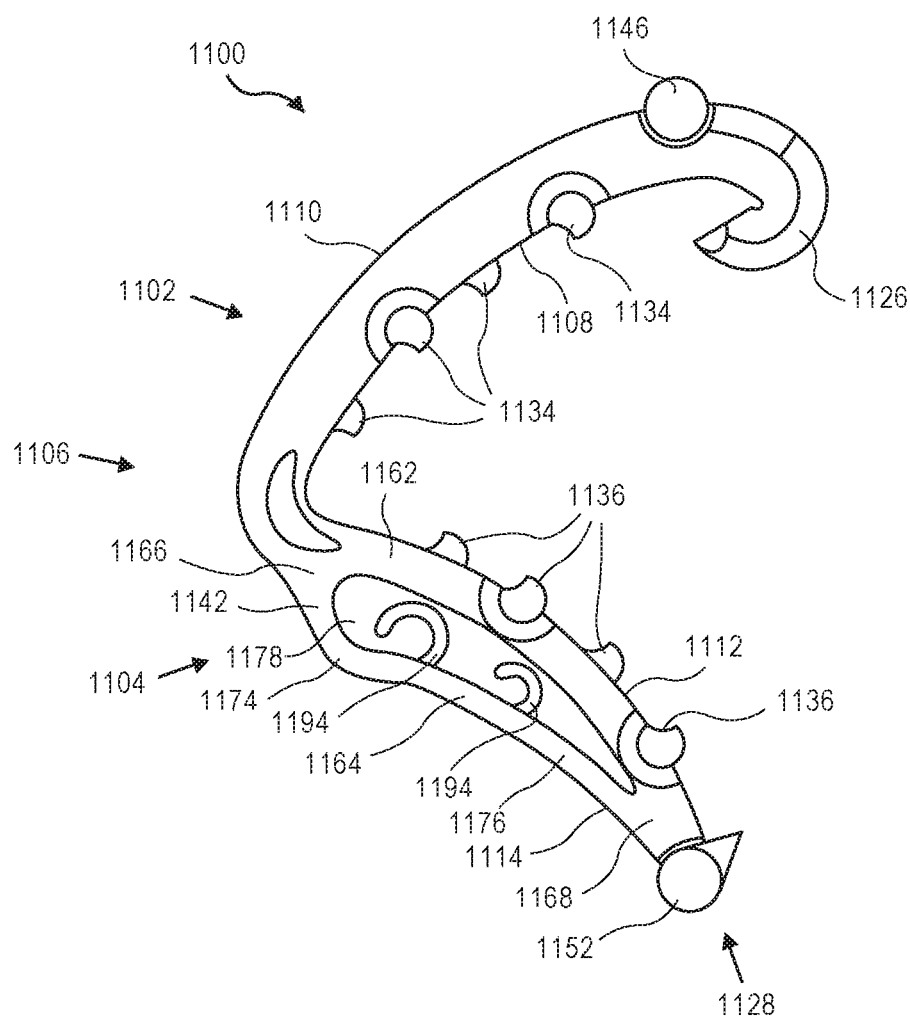
FIG. 23 illustrates a side view of an exemplary open configuration of an eleventh exemplary embodiment of the surgical clip of the present invention.

FIGS. 21-23 illustrate side views of additional embodiments of surgical clips 900-1100 of the present invention. The surgical clips 900-1100 may include one or more compression members 990, 1092, 1194 extending between inner and outer portions. The compression members 990, 1092, 1194 may allow for additional flexibility to the surgical clip, without substantially reducing overall compression strength of the surgical clip. In some applications, the strength of the surgical clip may vary depending on how much material the surgical clip is closed over. For example, the surgical clip may have a reduced compression strength if the gap between the inner and outer portions was not fully compression. The compression members 990, 1092, 1194 may be configured to improve compressive load distribution between the inner and outer portions, while maintaining flexibility and accommodating the complex deformation that the surgical clip goes through to close and/or lock. The compression members 990, 1092, 1194 may be resilient and support the inner portion to ensure sufficient compression through the length of the surgical clip. Although illustrated with the first embodiment of FIGS. 1-6, any one or more of the embodiments of the compression members 900, 1092, 1194 may be applied to any of the embodiments of the surgical clips 100-1100 of the present invention.

FIG. 21 illustrates a ninth embodiment of a surgical clip 900 of the present invention. The surgical clip 900 may include one or more features similar to at least one of surgical clips 100-800, and may be similarly represented in FIG. 21. For the sake of brevity, features similar to those of at least one of surgical clips 100-800 may not be discussed with reference to the surgical clip 900.

As illustrated, the surgical clip 900 may include a first leg member 902 and a second leg member 904 connected by a hinge portion 906. The first and second leg members 902, 904 may include surfaces having curved portions. For example, the first leg member 902 may include a first inner surface 908 and a first outer surface 910, and the second leg member 904 may include a second inner surface 912 and a second outer surface 914. The first inner surface 908 may have a concave curvature, and the first outer surface 910 may have a convex curvature. The second inner surface 912 may have a convex curvature, and the second outer surface 914 may have one or more of at least one convex curvature and/or at least one concave curvature. The first and second inner surfaces 908, 912 may be approximated or contact in a closed configuration. The first and second inner surfaces 908, 912 may be substantially smooth.

The second leg member 904 may include an inner portion 962 (e.g., an inner rib) and an outer portion 964 (e.g., an outer rib) separated by at least one transverse aperture or channel 978 and integrally joined at a first portion 966 and a second portion 968. The inner portion 962 and the outer portion 964 may have different radii of curvature between adjacent corresponding points along the length of the inner and outer portions 962, 964. In some embodiments, a first radius of curvature of the inner portion 962 and a second radius of curvature of the outer portion 964 may be different for at least half of the lengths of the inner and outer portions 962, 964. In some embodiments, the first radius of curvature and the second radius of curvature may be different for substantially the entire length of the inner and outer portions 962, 964. The inner portion 962 may have a substantially continuous radius of curvature without any points of inflection, and the outer portion 964 may have a variable radius of curvature with at least one point of inflection. The variable radius of curvature of the outer portion may provide a variable height and vertical stability when positioned in a feeding channel 12 of a clip applier 10, as illustrated in FIG. 5. For example, a proximal portion 974 of the outer portion 964 may have a greater height than a distal portion 976 of the outer portion 964. In some embodiments, the proximal portion 974 may include a convex outer surface and a concave inner surface, and the distal portion 976 may include a concave outer surface and a convex inner surface. The concave outer surface of the distal portion 976 may provide a smooth transition with the distal portion to reduce irregular stress concentrations. The convex outer surface of the proximal portion 974 may project vertically to provide a contact point with walls 14, 16 of the feeding channel 12 and reduce vertical movement of the proximal end of the surgical clip 900 relative to the clip applier 10. Additional contact points may include the outer surface 910 of the first leg member 902, the bosses 946, 948, and 950 of the first leg member 902, and/or the bosses 952, 954 of the second leg member 904. The increased vertical stability of the surgical clip 900 may ensure eliminate the need for a stability finger on a pusher member of the surgical clip applier 10 and/or proper loading of the surgical clip 900 into jaws of the clip applier 10.

The surgical clip may further include one or more compressions members 990 extending between the inner portion 962 and outer portion 964. As illustrated, the compression member 990 may comprise a single curved member integrally formed with an outer surface of the inner portion 962 and an inner surface of the outer portion 964. However, the compression member 990 may be integrally formed with only one of the inner portion 962 and outer portion 964 and releasably contact the other of the inner portion 962 and outer portion 964. The compression member 990 may extend through the channel 978 between a distal portion of the inner portion 962 to a proximal portion of the outer portion 964. For example, the compression member 990 may be joined or contact to a convex inner surface of the proximal portion 974 of the outer portion 964. As the surgical clip 900 is compressed, the compression member 990 may straighten and engage an increasing surface area of the inner portion 962 and/or outer portion 964, distributing the compressive load.

The surgical clip 900 may also include a latching mechanism having one or more latching elements. For example, the first leg member 902 may transition to a hook portion 926 at its distal end portion, and the second leg member 904 may transition to a complementary grooved and pointed tip portion 928 at its distal end portion. The leg members 902, 904 may further include one or more bosses along the length to engage the clip applier 10. For example, the first leg member 902 may include bosses 946, 948 protruding perpendicular to each of opposing side surfaces 938, 940, and the second leg member 904 may include bosses 952, 954 protruding perpendicular to each of the opposing sides 942, 944. The bosses 946, 948 of the first leg member 902 may be coupled together by a bridge section 950. As further shown in the embodiment of FIG. 21, the surgical clip 900 may include at least one first tooth 934 positioned on the first leg member 902, and at least one second tooth 936 positioned on the second leg member 904. The teeth 934, 936 may be substantially rigid, such that the teeth 934, 936 do not substantially deflect when engaging tissue. The teeth 934, 936 may be positioned out-board relative to the surgical clip 900, as discussed herein.

FIG. 22 illustrates a tenth embodiment of a surgical clip 1000 of the present invention. The surgical clip 1000 may include one or more features similar to at least one of surgical clips 100-900, and may be similarly represented in FIG. 22. For the sake of brevity, features similar to those of at least one of surgical clips 100-900 may not be discussed with reference to the surgical clip 1000.

As illustrated, the surgical clip 1000 may include a first leg member 1002 and a second leg member 1004 connected by a hinge portion 1006. The first and second leg members 1002, 1004 may include surfaces having curved portions. For example, the first leg member 1002 may include a first inner surface 1008 and a first outer surface 1010, and the second leg member 1004 may include a second inner surface 1012 and a second outer surface 1014. The first inner surface 1008 may have a concave curvature, and the first outer surface 1010 may have a convex curvature. The second inner surface 1012 may have a convex curvature, and the second outer surface 1014 may have one or more of at least one convex curvature and/or at least one concave curvature. The first and second inner surfaces 1008, 1012 may be approximated or contact in a closed configuration. The first and second inner surfaces 1008, 1012 may be substantially smooth.

The second leg member 1004 may include an inner portion 1062 (e.g., an inner rib) and an outer portion 1064 (e.g., an outer rib) separated by at least one transverse aperture or channel 1078 and integrally joined at a first portion 1066 and a second portion 1068. The inner portion 1062 and the outer portion 1064 may have different radii of curvature between adjacent corresponding points along the length of the inner and outer portions 1062, 1064. In some embodiments, a first radius of curvature of the inner portion 1062 and a second radius of curvature of the outer portion 1064 may be different for at least half of the lengths of the inner and outer portions 1062, 1064. In some embodiments, the first radius of curvature and the second radius of curvature may be different substantially the entire length of the inner and outer portions 1062, 1064. The inner portion 1062 may have a substantially continuous radius of curvature without any points of inflection, and the outer portion 1064 may have a variable radius of curvature with at least one point of inflection. The variable radius of curvature of the outer portion may provide a variable height and vertical stability when positioned in a feeding channel 12 of a clip applier 10, as illustrated in FIG. 5. For example, a proximal portion 1074 of the outer portion 1064 may have a greater height than a distal portion 1076 of the outer portion 1064. In some embodiments, the proximal portion 1074 may include a convex outer surface and a concave inner surface, and the distal portion 1076 may include a concave outer surface and a convex inner surface. The concave outer surface of the distal portion 1076 may provide a smooth transition with the distal portion to reduce irregular stress concentrations. The convex outer surface of the proximal portion 1074 may project vertically to provide a contact point with walls 14, 16 of the feeding channel 12 and reduce vertical movement of the proximal end of the surgical clip 1000 relative to the clip applier 10. Additional contact points may include the outer surface 1010 of the first leg member 1002, the bosses 1046, 1048, and 1050 of the first leg member 1002, and/or the bosses 1052, 1054 of the second leg member 1004. The increased vertical stability of the surgical clip 1000 may ensure eliminate the need for a stability finger on a pusher member of the surgical clip applier 10 and/or proper loading of the surgical clip 1000 into jaws of the clip applier 10.

The surgical clip may further include one or more compressions members 1092 extending between the inner portion 1062 and outer portion 1064. As illustrated, the compression members 1092 may comprise a plurality of curved members integrally formed with at least one of an outer surface of the inner portion 1062 and an inner surface of the outer portion 1064. The compression members 1092 may extend distally through the channel 978 from a plurality of locations of the outer surface of the inner portion 1062. As the surgical clip 1000 is compressed, the compression members 1092 may straighten and engage an increasing surface area of the inner portion 1062 and/or outer portion 1064, distributing the compressive load along the length of the inner portion 1062.

The surgical clip 1000 may also include a latching mechanism having one or more latching elements. For example, the first leg member 1002 may transition to a hook portion 1026 at its distal end portion, and the second leg member 1004 may transition to a complementary grooved and pointed tip portion 1028 at its distal end portion. The leg members 1002, 1004 may further include one or more bosses along the length to engage the clip applier 10. For example, the first leg member 1002 may include bosses 1046, 1048 protruding perpendicular to each of opposing side surfaces 1038, 1040, and the second leg member 1004 may include bosses 1052, 1054 protruding perpendicular to each of the opposing sides 1042, 1044. The bosses 1046, 1048 of the first leg member 1002 may be coupled together by a bridge section 1050. As further shown in the embodiment of FIG. 22, the surgical clip 1000 may include at least one first tooth 1034 positioned on the first leg member 1002, and at least one second tooth 1036 positioned on the second leg member 1004. The teeth 1034, 1036 may be substantially rigid, such that the teeth 1034, 1036 do not substantially deflect when engaging tissue. The teeth 1034, 1036 may be positioned out-board relative to the surgical clip 1000, as discussed herein.

FIG. 23 illustrates an eleventh embodiment of a surgical clip 1100 of the present invention. The surgical clip 1100 may include one or more features similar to at least one of surgical clips 100-1000, and may be similarly represented in FIG. 23. For the sake of brevity, features similar to those of at least one of surgical clips 100-1000 may not be discussed with reference to the surgical clip 1100.

As illustrated, the surgical clip 1100 may include a first leg member 1102 and a second leg member 1104 connected by a hinge portion 1106. The first and second leg members 1102, 1104 may include surfaces having curved portions. For example, the first leg member 1102 may include a first inner surface 1108 and a first outer surface 1110, and the second leg member 1104 may include a second inner surface 1112 and a second outer surface 1114. The first inner surface 1108 may have a concave curvature, and the first outer surface 1110 may have a convex curvature. The second inner surface 1112 may have a convex curvature, and the second outer surface 1114 may have one or more of at least one convex curvature and/or at least one concave curvature. The first and second inner surfaces 1108, 1112 may be approximated or contact in a closed configuration. The first and second inner surfaces 1108, 1112 may be substantially smooth.

The second leg member 1104 may include an inner portion 1162 (e.g., an inner rib) and an outer portion 1164 (e.g., an outer rib) separated by at least one transverse aperture or channel 1178 and integrally joined at a first portion 1166 and a second portion 1168. The inner portion 1162 and the outer portion 1164 may have different radii of curvature between adjacent corresponding points along the length of the inner and outer portions 1162, 1164. In some embodiments, a first radius of curvature of the inner portion 962 and a second radius of curvature of the outer portion 964 may be different for at least half of the lengths of the inner and outer portions 962, 964. In some embodiments, the first radius of curvature and the second radius of curvature may be different for substantially the entire length of the inner and outer portions 962, 964. The inner portion 1162 may have a substantially continuous radius of curvature without any points of inflection, and the outer portion 1164 may have a variable radius of curvature with at least one point of inflection. The variable radius of curvature of the outer portion may provide a variable height and vertical stability when positioned in a feeding channel 12 of a clip applier 10, as illustrated in FIG. 5. For example, a proximal portion 1174 of the outer portion 1164 may have a greater height than a distal portion 1176 of the outer portion 1164. In some embodiments, the proximal portion 1174 may include a convex outer surface and a concave inner surface, and the distal portion 1176 may include a concave outer surface and a convex inner surface. The concave outer surface of the distal portion 1176 may provide a smooth transition with the distal portion to reduce irregular stress concentrations. The convex outer surface of the proximal portion 1174 may project vertically to provide a contact point with walls 14, 16 of the feeding channel 12 and reduce vertical movement of the proximal end of the surgical clip 1100 relative to the clip applier 10. Additional contact points may include the outer surface 1110 of the first leg member 1102, the bosses 1146, 1148, and 1150 of the first leg member 1102, and/or the bosses 1152, 1154 of the second leg member 1104. The increased vertical stability of the surgical clip 1100 may ensure eliminate the need for a stability finger on a pusher member of the surgical clip applier 10 and/or proper loading of the surgical clip 1100 into jaws of the clip applier 10.

The surgical clip may further include one or more compressions members 1194 extending between the inner portion 1162 and outer portion 1164. As illustrated, the compression members 1194 may comprise a plurality of hook members integrally formed with at least one of an outer surface of the inner portion 1162 and an inner surface of the outer portion 1164. The compression members 1194 may extend through the channel 1178 from a plurality of locations of the outer surface of the inner portion 962. As the surgical clip 1100 is compressed, the compression member 1194 may flatten and engage an increasing surface area of the inner portion 1162 and/or outer portion 1164, distributing the compressive load the compressive load along the length of the inner portion 1162.

The surgical clip 1100 may also include a latching mechanism having one or more latching elements. For example, the first leg member 1102 may transition to a hook portion 1126 at its distal end portion, and the second leg member 1104 may transition to a complementary grooved and pointed tip portion 1128 at its distal end portion. The leg members 1102, 1104 may further include one or more bosses along the length to engage the clip applier 10. For example, the first leg member 1102 may include bosses 1146, 1148 protruding perpendicular to each of opposing side surfaces 1138, 1140, and the second leg member 1104 may include bosses 1152, 1154 protruding perpendicular to each of the opposing sides 1142, 1144. The bosses 1146, 1148 of the first leg member 1102 may be coupled together by a bridge section 1150. As further shown in the embodiment of FIG. 23, the surgical clip 1100 may include at least one first tooth 1134 positioned on the first leg member 1102, and at least one second tooth 1136 positioned on the second leg member 1104. The teeth 1134, 1136 may be substantially rigid, such that the teeth 1134, 1136 do not substantially deflect when engaging tissue. The teeth 1134, 1136 may be positioned out-board relative to the surgical clip 1100, as discussed herein.

The various embodiments of the surgical clip of the present invention may be made of any suitable size and may be applied to any number of tissues, such as blood vessels, lymph nodes, nerves, cystic ducts, or cardiac tissue. The various embodiments of the surgical clip may be constructed from any suitable biocompatible material, such as certain metals and polymers. However, the present invention is particularly suitable for practice with polymeric clips. Thus, the various embodiments of the surgical clip preferably comprises a one-piece integral polymeric body formed from a suitable strong biocompatible engineering plastic such as the type commonly used for surgical implants. Exemplary materials include homopolymer or co-polymer polyacetal, polyethylene terephthalate (PET), polybutylene terephthalate (PBT), polyoxymethylene, or other thermoplastic materials having similar properties that can be injection-molded, extruded or otherwise processed into like articles.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A surgical clip comprising:
   a first leg member having an inner surface, an outer surface, and first and second side surfaces, the inner surface of the first leg member having a curvature;
   a second leg member having an inner surface, an outer surface, and first and second side surfaces, the inner surface of the second leg member having a curvature; and
   at least one tooth on and extending from at least one of the first and second side surfaces of the second leg member, wherein the at least one tooth is configured to extend past the inner surface of the first leg member in a closed configuration.

2. The surgical clip of claim 1, wherein the at least one tooth includes at least one first tooth extending from the first side surface of the second leg member and at least one second tooth extending from the second side surface of the second leg member, and the at least one first tooth and the at least one second tooth are configured to receive the inner surface of the first leg member therebetween.

3. The surgical clip of claim 2, wherein the at least one first tooth and the at least one second tooth are staggered along the second leg member.

4. The surgical clip of claim 1, wherein the at least one tooth comprises a plurality of teeth longitudinally spaced out apart along the second leg member.

5. The surgical clip of claim 1, further comprising at least one tooth extending from at least one of the first and second side surfaces of the first leg member, wherein the at least one tooth of the first leg member is configured to extend past the inner surface of the second leg member in the closed configuration.

6. The surgical clip of claim 1, wherein the at least one tooth includes at least one substantially flat side surface.

7. The surgical clip of claim 1, wherein the at least one tooth includes first and second substantially flat side surfaces.

8. The surgical dip of claim 1, wherein the at least one tooth includes a convex or substantially flat inner surface.

9. The surgical dip of claim 1, wherein the inner surface of at least one of the first leg member and the second leg member is substantially smooth.

10. The surgical clip of claim 1, wherein the inner surface of the first leg member has a concave curvature, and the inner surface of the second leg member has a convex curvature.

11. The surgical clip of claim 1, further comprising:
    a hook member on a distal portion of the first leg member; and
    a tip member on a distal portion of the second leg member,
    wherein the hook member is configured to extend around the tip member in the closed configuration.

12. The surgical clip of claim 1, further comprising:
    a boss extending beyond at least one of the first and second side surfaces of the first leg member; and
    a boss extending beyond at least one of the first and second side surfaces of the second leg member.

13. The surgical clip of claim 1, further comprising a hinge portion connecting the first leg member and the second leg member.

14. A surgical clip comprising:
    a first leg member having an inner surface, an outer surface, and first and second side surfaces, the inner surface of the first leg member having a curvature;
    at least one first tooth extending from at least one of the first and second side surfaces of the first leg member;
    a second leg member having an inner surface, an outer surface, and first and second side surfaces, the inner surface of the second leg member having a curvature; and at least one second tooth extending from at least one of the first and second side surfaces of the second leg member, wherein the at least first one tooth is configured to extend past the inner surface of the second leg member in a closed configuration, and the at least one second tooth is configured to extend past the inner surface of the first leg member in the closed configuration.

15. The surgical clip of claim 14, wherein the at least one first tooth is on the at least one of the first and second side surfaces of the first leg member, and the at least one second tooth is on the at least one of the first and second side surfaces of the second leg member.

16. The surgical clip of claim 14, wherein the at least one first tooth extending from at least one of the first and second side surfaces of the first leg member includes:
at least one first tooth extending from the first side surface of the first leg member; and
at least one first tooth extending from the second side surface of the first leg member, wherein
the at least one first tooth extending from the first side surface of the first leg member and the at least one first tooth extending from the second side surface of the first leg member are configured to receive the inner surface of the second leg member therebetween.

17. The surgical clip of claim 14, wherein the at least one first tooth comprises a plurality of first teeth longitudinally spaced out apart along the first leg member, and the at least one second tooth comprises a plurality of second teeth longitudinally spaced out apart along: the second leg member.

18. The surgical clip of claim 17, wherein the plurality of first teeth and the plurality of second teeth are staggered.

19. The surgical clip of claim 14, further comprising:
a hook member on a distal portion of the first leg member; and
a tip member on a distal portion of the second leg member,
wherein the hook member is configured to extend around the tip member in the closed configuration.

20. The surgical clip of claim 14, further comprising:
a boss extending beyond at least one of the first and second side surfaces of the first leg member; and
a boss extending beyond at least one of the first and second side surfaces of the second leg member.

21. The surgical clip of claim 14, wherein the inner surface of the first leg member has a concave curvature, and the inner surface of the second leg member has a convex curvature.

22. The surgical clip of claim 14, wherein the inner surface of at least one of the first leg member and the second leg member is substantially smooth.

23. A surgical clip comprising:
a first leg member having an inner surface, an outer surface, and first and second side surfaces, the inner surface of the first leg member having a curvature;
a second leg, member having an inner surface, an outer surface, and first and second side surfaces, the inner surface of the second leg member having a curvature;
a plurality of first teeth longitudinally spaced out apart on the first side surface of the second leg member; and
a plurality of second teeth longitudinally spaced out apart on the second side surface of the second leg member,
wherein the plurality of first teeth and the plurality of second teeth are configured to extend past the inner surface of the first leg member in a closed configuration and receive the inner surface of the first leg, member therebetween.

24. The surgical clip of claim 23, further comprising:
a hook member on a distal portion of the first leg member; and
a tip member on a distal portion of the second leg member,
wherein the hook member is configured to extend around the tip member in the closed configuration.

25. The surgical clip of claim 23, further comprising:
a boss extending beyond at least one of the first and second side surfaces of the first leg member; and
a boss extending beyond at least one of the first and second side surfaces of the second leg member.

26. The surgical clip of claim 23, wherein the inner surface of the first leg member has a concave curvature, and the inner surface of the second leg member has a convex curvature.

27. The surgical dip of claim 23, wherein the inner surface of at least one of the first leg member and the second leg member is substantially smooth.

28. The surgical clip of claim 23, wherein the plurality of first teeth and the plurality of second teeth are staggered.

\* \* \* \* \*